United States Patent [19]
Maki et al.

[11] Patent Number: 5,678,556
[45] Date of Patent: Oct. 21, 1997

[54] IMAGING METHOD FOR SPATIAL DISTRIBUTIONS OF ABSORBER CONCENTRATIONS

[75] Inventors: Atsushi Maki, Hachioji, Japan; Adi Bonen, Willowdale, Canada; Yoshitoshi Ito, Ome, Japan; Yuichi Yamashita, Hachioji, Japan; Yukiko Hirabayashi, Kokubunji, Japan; Hideaki Koizumi, Tokyo, Japan; Fumio Kawaguchi; Hideji Fujii, both of Hinode-Machi, Japan

[73] Assignee: Hitachi, Ltd., Tokyo, Japan

[21] Appl. No.: 502,844

[22] Filed: Jul. 14, 1995

[30] Foreign Application Priority Data

Jul. 14, 1994 [JP] Japan .................................. 6-161823

[51] Int. Cl.⁶ .................................................. A61B 6/00
[52] U.S. Cl. .................................................. 128/665
[58] Field of Search .................................. 128/664, 665; 356/342

[56] References Cited

U.S. PATENT DOCUMENTS 5,137,355   8/1992   Barbour et al. .................... 356/342

FOREIGN PATENT DOCUMENTS

| 57-115232 | 7/1982 | Japan . |
| 63-275323 | 11/1988 | Japan . |
| 1-209342 | 8/1989 | Japan . |
| 3-505922 | 12/1991 | Japan . |
| WO 91/07655 | 5/1991 | WIPO . |
| WO 93/133 | 7/1993 | WIPO . |

OTHER PUBLICATIONS

SPIE 1431, pp. 204–215 "Reconstruction methods for infra-red absorption imaging" (1991).
Science, vol. 248, pp. 990–993 "Image Reconstruction of the Interior of Bodies That Diffuse Radiation" (1990).
Medical Optical Tomography: Functional Imaging and Monitoring, vol. 1s11, pp. 121–143 (1993).
BBA 42733, "Characterization of the near infrared absorption spectra of cytochrome aa3 and haemoglobin for the noninvasive . . ." pp. 184–192 (1988).
Am. Assoc. Phys. Med. vol. 10 (1983) "A Monte Carlo model for the absorption and flux distributions of light in tissue" pp. 824–830.
Journal of the Optical Society of America vol. 60 No. 8, (1970) "Absortion and Multiple Scattering by Biological Suspensions" pp. 1084–1093.
"Image reconstruction of the Interior of Bodies that Diffuse Radiation", Singer, et al, Science, vol. 248, May 25, 1990, pp. 990–993.

*Primary Examiner*—Marvin M. Lateef
*Assistant Examiner*—Eleni Mantis Mercader
*Attorney, Agent, or Firm*—Antonelli, Terry, Stout & Kraus, LLP.

[57] ABSTRACT

An imaging method for spatial distributions of concentrations of absorbers distributed in an object including a radiation step of applying pulsating or continuous light radiated from predetermined incident positions with predetermined wavelengths to the object in the form of a scattering medium containing the absorbers, and a detection step of detecting intensities of light passing through the object at predetermined detection positions. The imaging method also includes a step of finding a plurality photon paths for a plurality of pairs of the incident and detected positions of a model with similar dimensions to the object but without absorbers starting at the incident positions and ending at the detected positions, a step of finding averaged photon-path lengths of the photon paths starting at the incident positions and ending at the detection positions in the model by simulation, a step of finding spatial distributions of absorber concentrations from the averaged photon-path lengths, radiated intensities of the radiated light applied to the object, detected intensities of light detected at the detection positions and optical constants of the absorbers for the radiated light applied to the object, and a step of displaying the spatial distributions of the absorber concentrations.

26 Claims, 20 Drawing Sheets

SPATIAL RESOLUTION
(FULL WIDTH HALF MAXIMUM)
|← 15mm →|

IMAGING METHOD FOR SPATIAL DISTRIBUTIONS OF ABSORBER CONCENTRATIONS

BACKGROUND OF THE INVENTION

The present invention relates to a technique for finding concentrations of absorbers existing in an object comprising a scattering medium containing the absorbers. In particular, the present technique relates to a method as well as a device for finding spatial distributions of concentration of absorbers in a human body or in the air by using light.

At the present time, an MRI (Magnetic Resonance Imaging device), an X-ray CT and an ultrasonic diagnostic device and the like, are available for use as an imaging diagnostic device in the medical-care field. In the field of clinical medicine, on the other hand, many of these devices are used on the spot and proven useful. At the present time, there are a number of imaging diagnostic devices that are used in the clinical-medicine field for obtaining information on mainly tissues and structures in a human body as a tomographic image. However, there are only few handy and practical imaging diagnostic devices that can be used for measuring biological functions resulting from the metabolism of chemical substances distributed throughout a human body. Information obtained by measurement of the biological functions is expected to be useful for preventive diagnoses of brain diseases and cancers and the clarification of brain functions. The development of handy and practical imaging diagnostic devices for measuring biological functions is expected in the field of medicine.

There is a living-body optical measurement device for producing an image of the spatial distribution of the specific-pigment concentration in a human body. It is used as an optical measurement device for producing an image of the spatial distribution of the concentration of an absorber in an object wherein the absorber exists in a scattering medium, exhibiting absorption characteristics which vary, depending upon the wavelength of the light used in the measurement. In a human body, there are a number of absorbers which participate in biological functions. The development of an optical measurement device capable of measuring the spatial distribution of the concentration of such an absorber as one of tools for producing images of the biological functions and useful for diagnoses is carried out in a hurry.

Among the biological functions, the oxygen saturation in a human body corresponds to the concentration of a large number of specific pigments existing in the human body. This concentration of the specific pigments can be measured from the amount of optical absorption in regions of light ranging from the visible light to the near-infrared light. The specific pigments are known to have spectral characteristics which differ from each other, depending on whether the pigment is of an oxygenated type or a deoxygenated type. There are a variety of specific pigments such as the hemoglobin in the blood which hemoglobin is referred to hereafter as Hb, the cytochrome aa3 existing in the cell and the myoglobin existing in the muscle. By further utilizing optical fibers and a small-size light source in the optical measurement, the development of a handy and compact device becomes possible.

Devices for measuring biological functions by using visible to near-infrared light are disclosed in documents such as Japanese Patent Laid-open Nos. Sho 57-115232 and Sho 63-275323. An important challenge encountered in the optical measurement device is the establishment of a technique for producing an image of the spatial distribution of the concentration of an absorber existing in a human body. The challenge is how to solve a problem as to the locations and concentrations of the absorbers to be found. Imaging methods utilizing the conventional technology can be classified into three major categories: (1) techniques adopting the algorithm of the X-ray CT, (2) techniques based on a transport equation and (3) techniques based on results of simulation using the Monte Carlo method.

An actual example of the first-category techniques is a method of obtaining an image by means of an image reconstructing algorithm used in the X-ray CT from measurement data obtained by using a time-gate method. This method is disclosed in Japanese Patent Laid-open No. H01-209342.

Actual examples of the second-category techniques include a method proposed by Aridge et al. and a method proposed by Singer et al. The former is described in Proc. SPIE 1431, pages 204 to 215 (1991) as an article with the title "Reconstruction Methods for Infrared Absorption Imaging," whereas the latter is described in Science, 248, pages 990 to 993 (1990) as an article with the title "Image Reconstruction of Bodies That Diffuse Radiation."

Actual examples of the third-category techniques are imaging methods based on the Monte Carlo method proposed by Randall L. Barbour. The examples are disclosed in Japanese Patent Laid-open No. H3-505922 and described as an article with the title "A Perturbation Model for Imaging in Dense Scattering Media: Derivation and Evaluation of Imaging Operators," in Medical Optical Tomography: Functional Imaging and Monitoring, Volume IS11, pages 121 to 143 (1993).

The optical measurement device displays the spatial distribution of the concentration of an absorber, which functions in a human body, such as Hb (the hemoglobin) as an image. Its application to preventive diagnoses of a variety of diseases such as the cancer is expected. Since a human body exhibits a strong scattering characteristic with a scattering parameter of about 1.0 mm-1 against light, however, it is extremely difficult to obtain an image of the spatial distribution of the concentration of an absorber existing in a human body with a high degree of accuracy. In order to put the optical measurement device to practical use in the clinical-medicine field, a technique for obtaining accurate images for spatial distributions of concentrations of absorbers existing in a variety of scattering media such as a human body is required. At the present time, an imaging technique for the spatial distribution of the concentration of an absorber in a human body, which technique is considered to have achieved the practical-usage level, does not exist yet.

A variety of problems exist in the methods adopting the conventional technologies. In the first-category techniques, the spatial resolution of an image reconstructed for treating a three-dimensional phenomenon in a two-dimensional space is low. In the second-category techniques, time consuming processing for executing repetitive calculations is required, making it virtually difficult to produce an image with a high degree of resolution at the speed of a computer of the present state of the art. In addition, in some cases, an optimal solution is difficult to obtain due to a fall-in into a local minimum. In the third-category techniques, there is description stating three-dimensional conversion of a target object existing in an opaque medium into an image. However, an actual imaging procedure is not shown numerically or clearly. In addition, there is no description as to how the concentration of an absorber existing in the medium is calculated.

SUMMARY OF THE INVENTION

It is an object of the present invention to provide a technique and a device for finding three-dimensional spatial distributions of concentrations of absorbers functioning in a human body by taking three-dimensional scattering phenomena into consideration and, in particular, accurately calculating the concentration of the absorber at a spatial-resolution level and in a short period of time.

The technique and device provided by the present invention are characterized in that three-dimensional distributions of concentrations of absorbers existing in an object are found by assuming that the intensity of a light detected after passing through the object can be expressed as a linear function of concentrations of absorbers and averaged photon-path lengths of photons experiencing scattering and by using a spatial distribution of the averaged photon-path lengths. Namely, the present invention provides a technique for producing images of spatial distributions of concentrations of absorbers distributed in an object composed of a scattering medium containing the absorbers comprising: a radiation step of applying pulsating light or continuous light radiated from predetermined incident positions with predetermined wavelengths to the object; and a detection step of detecting the intensities of light passing through the object at predetermined detection positions; which technique is characterized in that: a plurality of photon paths starting at the incident positions and ending at the detection positions are found; averaged photon-path lengths are found from the photon paths; and concentrations of the absorbers are calculated for each volume element also referred to hereafter as a voxel from the averaged photon-path lengths, the intensities of the radiated light applied to the object, the intensities of the light detected at the detection positions and optical constants of the absorbers for the radiated lights applied to the object.

A spatial distribution of averaged photon-path lengths is calculated by simulation using the Monte Carlo method. This calculation is also used to find a plurality of photon paths traced by a plurality of photons originating from a point in a model scattering medium which has virtually the same scattering coefficient as that of the real object and a size large enough to contain a model object. It should be noted that a model object has a shape identical with or similar to that of the real object but does not contain an absorber.

In more detail, the technique for producing images of the spatial distributions of absorbers' concentrations provided by the present invention is characterized in that the technique comprises the steps of: finding a plurality of photon paths each traced by a photon starting at an incident position and ending at a detection position for each of a plurality of pairs of such incident and detection positions set in a model object not including an absorber and having a shape identical with or similar to that of an object; finding averaged photon-path lengths from the photon paths starting at incident positions and ending at detection positions in the model object;

finding spatial distributions of concentrations of the absorbers from the averaged photon-path lengths, intensities of incident light applied to the object, intensities of the light detected at detection positions and optical constants (or absorption coefficients) of the absorbers for the incident light applied to the object; and displaying spatial distributions of concentrations of the absorbers.

A space which the shape of the object fits is divided into a plurality of volume elements. For each volume element, an averaged photon-path length is found and, by assuming that the concentrations of the absorbers in a volume element are uniform, the concentrations of the absorbers in each volume element are found.

The actual process to produce an image of the spatial distribution of an absorber's concentration comprises the steps of: creating a measurement matrix each calculated from a ratio of the intensity of a light radiated at an incident position to the intensity of a light detected at a detection position which incident and detection positions constitute a pair described above; creating a matrix expressing a spatial distribution of averaged photon-path lengths each calculated from an averaged photon-path length for a pair of incident and detection positions described above; and finding concentrations of the absorbers from the measurement matrix and the matrix expressing a spatial distribution of averaged photon-path lengths.

When the procedure provided by the present invention is applied to an object which has a predetermined shape and scattering coefficients given in advance, a matrix expressing a spatial distribution of averaged photon-path lengths which has already been found at the aforementioned step of creating a matrix expressing a spatial distribution of average photon-path lengths and stored in a storage means is used.

At the step of finding photon paths, a photon path is found by simulation based on the Monte Carlo method. With the Monte Carlo method, a photon path traced by a photon originating from a point in a model scattering medium, which has virtually the same scattering coefficient as the real object and a size large enough to contain an imaginary object, is found. In the Monte Carlo method, a function expressing scattering-angle dependence and a random number are used. The function expressing scattering-angle dependence provides a relation between the spatial-coordinate positions of two consecutive scattering points among a plurality of scattering points, a photon is scattered from one scattering point to a next scattering point of two consecutive points. The spatial-coordinate positions of the scattering points, which represent each of the photon paths found by using the Monte Carlo method, are stored in the storage means. Data of the photon paths is stored in the storage means. Each piece of the photon-path data represents either the length of a limited photon path traced by a single photon originating from a point in the model scattering medium or the lengths of photon paths in a sphere used as a model scattering medium among all photon paths traced by a plurality of photons originating from the center of the sphere, wherein the sphere has a radius greater than a maximum distance from an arbitrary point to another arbitrary one in the model object.

A photon path starting from an incident position in a model object and ending at a detection position is determined with a point at the model scattering medium used as the incident position at the model object and a cross-point of the detection plane and a photon path found by the Monte Carlo method used as the detection position. The photon path is then found by transformation of either the spatial coordinates of the scattering points expressing the photon path or the spatial coordinates expressing the shape of the model object into the other spatial coordinates. The coordinate transformation can be a rotation or translation shift of the coordinates. A plurality of photon paths starting from incident positions and ending at detection points at the model object, which photon paths are found as described above, are each treated as a photon path between corresponding incident and detection positions at the object. It should be noted that a space expressing the shape of a model object is divided into a plurality of volume elements in the same way as a space expressing the shape of an object is divided into a plurality of volume elements. In addition, the number of incident-position and detection-position pairs is set at a value greater than the total number of volume elements constituting the space expressing the shape of a model object or the space expressing the shape of an object.

From the data of the photon paths, an averaged photon-path length for each volume element in the model object can be found by averaging the lengths of photon paths in the volume element. The result is treated as an average photon-path length for each volume element in the object. Let (i-j) be a pair of incident position i and detection position j and (j-i) be a pair of incident position j and detection position i. The latter pair is obtained by swapping the incident and detection positions of the former pair for each other. Data of a photon path of the latter pair can be found from data of a photon path of the former pair by coordinate transformation.

Incident light applied to the object at the radiation step have a plurality of different wavelengths having values in the range 400 to 2,000 nm. The difference in value between any two of the wavelengths are made smaller than 100 nm. In a time-resolving measurement of the intensity of a light, the intensity of a detected light is obtained by integration of light intensities resulting from the time-resolving measurement which integration is taken over a predetermined period of time. Averaged photon-path lengths computed from lengths of photo paths of photons arriving at detection positions from incident positions within the predetermined period of time are used for creating a matrix expressing a spatial distribution of averaged photon-path lengths.

The technique provided by the present invention comprises the steps of: creating a measurement matrix Y calculated from the measured intensities of detected light; finding data for photon paths of light passing through a scattering medium from the absorption coefficients of absorbers in the scattering medium which photon paths are obtained by simulation of the scattering medium not containing an absorber using the Monte Carlo method;

creating a matrix A expressing a spatial distribution of averaged photon-path lengths calculated from the photon-path data; deriving an unknown matrix X of unknown quantities from the matrices Y and A; finding concentrations of the absorbers in the object from the unknown matrix X; and displaying a spatial distribution of the concentrations.

In addition, the number of pairs of incident and detection positions provided at a plurality of different locations is set at a value greater than the total number of volume elements constituting the space expressing the shape of a model object or the total number of volume elements composing the space expressing the shape of an object. Accordingly, effects of scattering from a plurality of directions are taken into consideration when paying attention to a certain volume element. As a result, it is possible to obtain a three-dimensional spatial distribution of the concentration of an absorber which distribution has a spatial resolution more than three times better than that of the conventional technique and to shorten the computation time by about 10 to 100 times. On top of that, the quantitative accuracy can also be improved as well. With this technique, a solution can be obtained without a fall-in into a local optimum solution. When photon-path data calculated in advance is stored in a storage means, a photon path is calculated by means of the Monte Carlo method using the photon-path data stored in the storage means, allowing a spatial distribution of averaged photon-path lengths to be produced at a speed about more than 100 times higher than that of the technique adopting the conventional Monte Carlo method. In this way, by virtue of the technique provided by the present invention, the spatial resolution and the quantitative accuracy can be improved over those provided by the conventional method.

As described in a summary shown in FIG. 15, the imaging method for the spatial distributions of the concentrations of absorbers provided by the present invention comprises: a step 1 of creating a measurement matrix calculated from measured intensities of detected light; a step 2 of finding data for photon paths of light passing through a scattering medium from absorption coefficients of an absorber in the scattering medium, which photon paths are obtained by simulation of a scattering medium containing no absorber by using the Monte Carlo method, and then creating a matrix A expressing a spatial distribution of averaged photon-path lengths calculated from the photon-path data; a step 3 of deriving a matrix X of unknown quantities from the matrices Y and A and then finding the concentration of the absorber in the object from the unknown matrix X; and a step 4 of displaying a spatial distribution of the concentration.

When photon paths have been calculated by using the Monte Carlo method prior to the start of the processing carried out at the step 2 and results have been stored in a storage means, the stored photon-path data is used instead of finding data for the photon paths.

DESCRIPTION OF THE PREFERRED EMBODIMENTS

There is an optical measurement device adopting the conventional technology for measuring a spatial distribution of the concentration of specific pigments distributed in a human body which device utilizes light for the measurement. In addition, a laser radar is available as an instrument for measuring a spatial distribution of the concentration of an absorber existing in the air. For this reason, a technique for finding a spatial distribution of the concentration of an absorber existing in a scattering medium and producing an image of the spatial distribution is required in a variety of fields. A representative example of the optical measurement device is described as follows.

Figure 1:
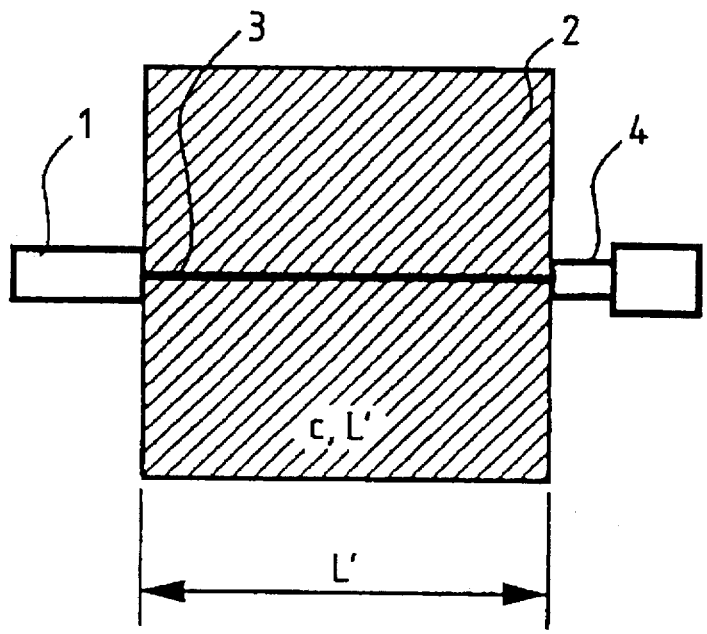
FIG. 1 is a diagram showing a cross section including a photon path in an object comprising an absorber contained uniformly to which the present application is applied.

First of all, a case in which the incident light is not scattered by an object or a case in which the object is a non-scattering material is explained. The explanation is followed by description of a case in which the incident light is scattered by an object or a case in which the object is a scattering material. As shown in FIG. 1, a light radiated from a light source 1 is applied to an object 2. Let us think of an optical measurement system for detecting the intensity of a light tracing a photon path 3 by means of a detector 4. FIG. 1 is a diagram showing a cross section of the object 2 including the photon path 3. Beer Lambart's law defined by Equation (1) holds true as follows:

$$I_d/I_0 = \exp(-\epsilon c L') \tag{1}$$

where c is a uniform concentration of an absorber existing as a single element in the object 2, $I_0$ is the intensity of a light radiated by the light source 1, $I_d$ is the intensity of a light detected by the detector 4, $\epsilon$ is the molecular extinction coefficient of the absorber and L' is the photon-path length which is determined by a geometrical distance from the incident position to the detection position.

Figure 2:
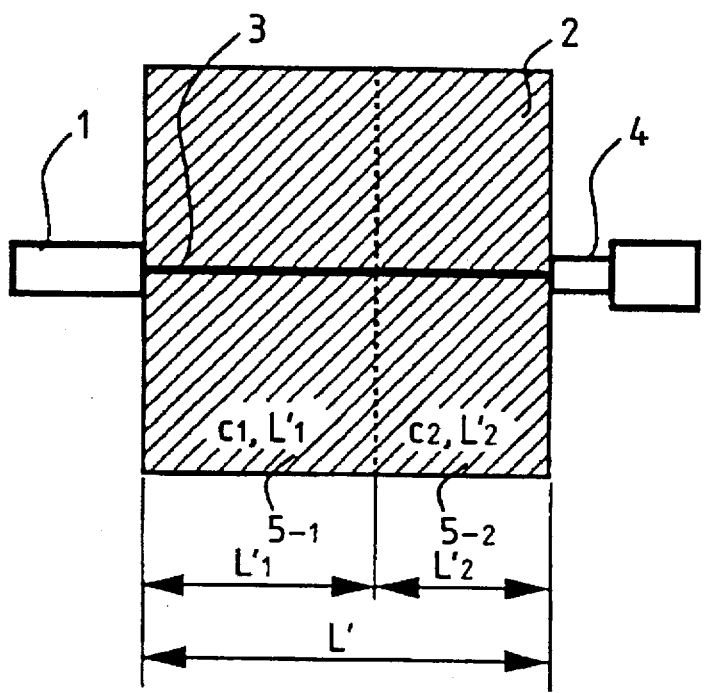
FIG. 2 is a diagram showing a cross section including a photon path in an object comprising an absorber composed of two different layers to which the present application is applied.

Now, let us consider an optical measurement system of FIG. 2 similar to that shown in FIG. 1. As shown in FIG. 2, an object 2 is divided into two volume elements 5-1 and 5-2 with absorber concentrations different from each other. Let $c_1$ and $L_1'$ be the absorber concentration and the photon-path length in the volume element 5-1 respectively whereas $c_2$ and $L_2'$ be the absorber concentration and the photon-path length in the volume element 5-2 respectively. Equations (2) and (3) are obtained by deriving them from Equation (1) for the volume elements 5-1 and 5-2 respectively:

$$I_c/I_0 = \exp(-\epsilon c_1 L_1') \tag{2}$$

$$I_d/I_c = \exp(-\epsilon c_2 L_2') \tag{3}$$

where $I_0$ is the intensity of a light radiated by the light source 1, $I_c$ is the intensity of an incident light from the volume element 5-1 hitting the volume element 5-2 and $I_d$ is the intensity of a light detected by the detector 4. Since the intensity $I_c$ of the incident light from the volume element 5-1 hitting the volume element 5-2 is not measured, it can be eliminated. Equation (4) is derived by elimination of $I_c$ from Equations (2) and (3) as follows:

$$I_d/I_0 = \exp(-\epsilon(c_1 L_1' + c_2 L_2')) \tag{4}$$

Next, a case in which the object is a scattering material is explained. Unless specified otherwise, the object used in the following description is a scattering material.

Figure 3:
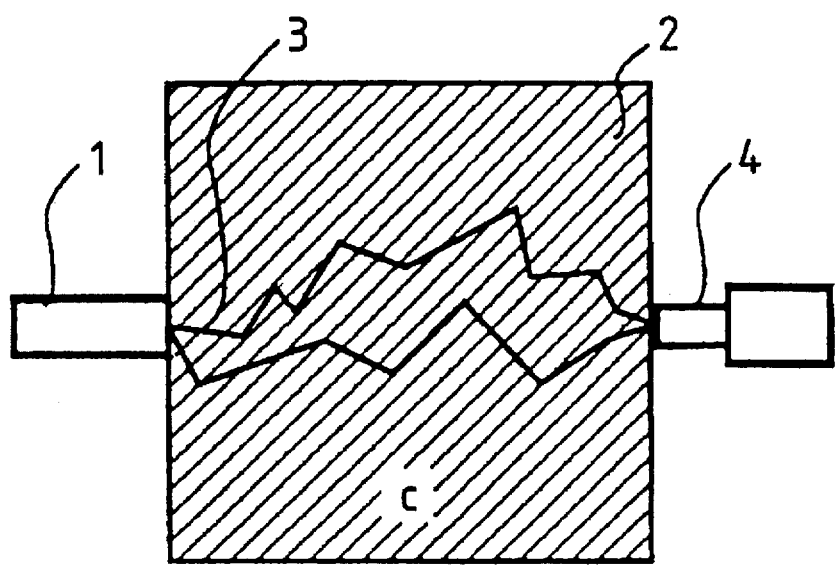
FIG. 3 is a diagram showing a cross section including photon paths in an object comprising a scattering medium and an absorber contained in the scattering medium uniformly to which the present application is applied.

In an optical measurement system shown in FIG. 3, an absorber with a uniform concentration c exists as a single element in the object 2. In this case, the following Equation (5) holds true:

$$I_d/I_0 = D_s \exp(-\epsilon c L) \tag{5}$$

where $I_0$ is the intensity of a light radiated by the light source 1, $I_d$ is the intensity of a light detected by the detector 4, $\epsilon$ is the molecular extinction coefficient of the absorber, L is the photon-path length for an object not containing an absorber which length is referred to hereafter merely as the photon-path length and $D_s$ is an attenuation constant reflecting components going out off the object 2. For details, refer to "Absorption and Multiple Scattering by Biological Suspensions," written by Victor Twersky, in J. Opt. Soc. Am., 60, 1,089 (1970). Here, light is treated as photons which are radiated from the light source 1 and then scattered repeatedly in the object 2 before arriving at the detector 4. The onward-movement direction of a photon is changed each time the photon is scattered, resulting in a zigzag photon path 3 like the ones shown in FIG. 3. It should be noted that, much like those shown in FIGS. 1 and 2, the object 2 shown in FIG. 3 is a solid body. For the sake of simplicity, however, two photon paths 3 are shown in FIG. 3 on a cross-sectional plane. In general, a photon path 3 has a three-dimensional zigzag form. Changes in onward-movement direction caused by scattering are random, resulting in the photon paths 3 which differ from photon to photon. Therefore, a plurality of photon-path lengths L in Equation (5) exist and, hence, can not be determined univocally. For this reason, an averaged value of the photon-path lengths, which is referred to hereafter as an averaged photon-path length, is used as an approximate value. Let the number of photons arriving at the detector be m. In this case, the number of photon paths is also m. Let $L_k$ be the length of the kth photon path. The averaged photon-path length $L_A$ is defined by Equation (6) as follows.

$$L_A = (\Sigma L_k)/m \qquad (6)$$

where the symbol $\Sigma$ in the above equation denotes summation carried out for k=1 to m.

By further substituting the averaged photon-path length $L_A$ into Equation (5), Equation (7) can be derived as follows.

$$I_d/I_0 = D_s \cdot \exp(-\epsilon c L_A) \qquad (7)$$

Figure 4:
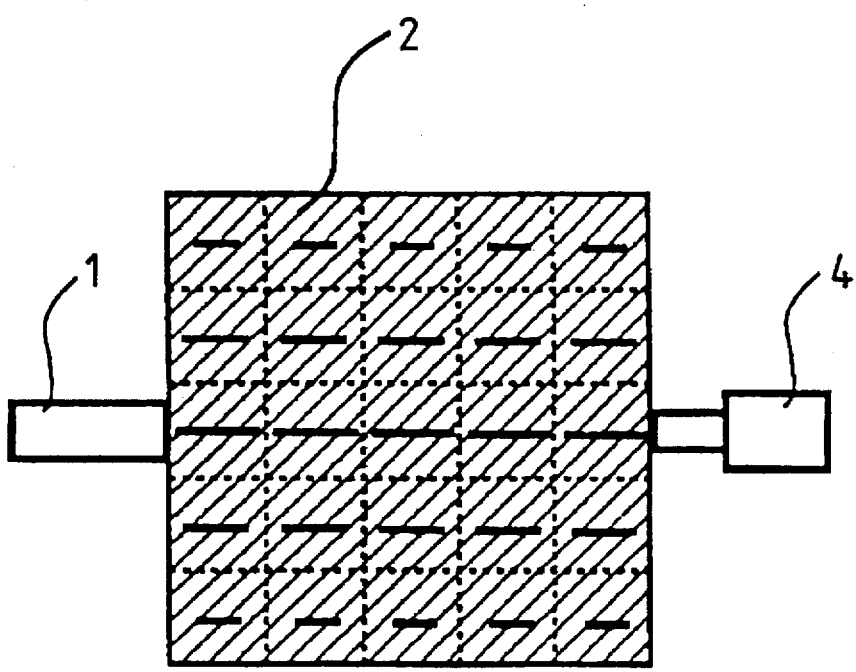
FIG. 4 is a model diagram showing a photon path in each of a plurality of volume elements constituting an object comprising a scattering medium and an absorber contained in the scattering medium to which the present application is applied.

Let us think of division of the object 2 of the optical measurement system shown in FIG. 3 into n volume elements as shown in FIG. 4. Assume that photons generated by the light source 1 pass through all the volume elements, arriving at the detector 4. Furthermore, the absorber concentration is considered to be, in general, different from volume element to volume element. Much like those shown in FIG. 3, for the sake of simplicity, all photon paths traced by photons which are radiated by the light source 1, arriving at the detector 4 after being scattered in the object 2 repeatedly are on a cross-sectional plane with a thickness equal to that of a volume element as shown in FIG. 4. The photon paths existing on the cross-sectional plane are each considered to comprise path segments in each volume element, which path segments have onward-movement directions different from each other. The lengths of path segments composing a photon path, which path segments pertain to a volume element, are added up to give a total which is then divided by a constant value. The result of the division is a photon-path length denoted by a thick line segment shown in the middle of the volume element of interest, which line segment is parallel to a straight line connecting the light source 1 to the detector 4. It should be noted that, for each volume element, the total is divided by a constant value so that the maximum of photon-path lengths for all the volume elements is smaller than the length of the side of the volume element. In other words, a two-dimensional body shown in FIG. 4 is assumed as the object 2 which is considered to comprise spatial (area) elements known as pixels. A plurality of photons from the source light 1 each move forward, forming a photon path. While a photon is moving forward, it is scattered on the two-dimensional plane, and its onward-movement direction of the photon path is changed. The lengths of path segments pertaining to an area segment are added up to produce a sum which is then divided by a constant to result in a photon-path length which is denoted by a thick line segment parallel to the straight line connecting the light source 1 to the detector 4. In the case of a uniform scattering medium containing no absorber, the distribution of the lengths of the thick line segments is symmetrical to the straight line connecting the light source 1 to the detector 4 and, the longer the distance from the straight line to a thick line segment, the shorter the length of the thick line segment as shown in FIG. 4. In general, however, the object 2 is not a uniform scattering medium. As a result, in such a general case, the thick line segments shown in FIG. 4 have lengths which are different from area element to area element.

In the present invention, a plurality of photons originating from the light source 1 are assumed to generally each pass through all volume elements composing the object 2. By regarding that an object comprises volume elements which are each shown in FIG. 3, Equation (7) can be applied thereto. Equation (4) which is applicable to a plurality of absorbers with concentrations different from each other can, on the other hand, be applied. That is, if we assume that a plurality of photons originating from the light source 1 each move forward, tracing a zigzag path due to scattering and pass through all volume elements before reaching the detector 4, Equation (8) given below holds true when Equations (4) and (7) are taken into consideration:

$$\begin{aligned}I_d/I_0 &= D_s \cdot \exp(-\epsilon(c_1 L_{A1} + + \ldots + c_n L_{An})) \\ &= D_s \cdot \exp(-\epsilon \Sigma(c_j L_{Aj}))\end{aligned} \qquad (8)$$

where $c_j$ is the absorber concentration in a volume element, $L_{Aj}$ is the averaged photon-path length in a volume element, the subscript j of $c_j$ and $L_{Aj}$ denotes the jth volume element to which the absorber concentration and the averaged photon-path length pertain respectively and $\Sigma$ indicates summation carried out for j=1 to n, the total number of volume elements. In the example shown in FIG. 4, the total number of volume elements (n) is 5×5=25. It should be noted that a photon is assumed to generally pass through all volume elements composing an object. For a volume element which no photon passes through, $L_{Aj}=0$. Since a technique for finding the averaged photon-path length $L_{Aj}$ (j=1 to n) for each volume element will be described later, here, $L_{Aj}$ (j=1 to n) is treated as a known quantity. It is difficult to directly find the attenuation constant $D_s$. Therefore, $D_s$ is eliminated by a technique of measurement wherein two kinds of light with wavelengths different from each other are used as radiated beams in two measurements. Equations (9) and (10) hold true for the two measurements using different incident light with wavelengths $\lambda_1$ and $\lambda_2$ respectively. In the equations, the averaged photon-path length $L_{Aj}$ is assumed to be independent of the wavelength. On the other hand, $D_s$ and $\epsilon$ are each a function of wavelength.

$$I_d(\lambda_1)/I_0(\lambda_1) = D_s(\lambda_1) \cdot \exp(-\epsilon(\lambda_1)\Sigma(c_j L_{Aj})) \qquad (9)$$

$$I_d(\lambda_2)/I_0(\lambda_2) = D_s(\lambda_2) \cdot \exp(-\epsilon(\lambda_2)\Sigma(c_j L_{Aj})) \qquad (10)$$

In Equations (9) and (10), denotes summation carried out for j=1 to n.

By variable transformation using Equations (11) and (12), Equations (9) and (10) are converted into Equations (13) and (14) as follows.

$$\mu(j, \lambda_1) = \epsilon(\lambda_1) c_j \qquad (11)$$

$$\mu(j, \lambda_2) = \epsilon(\lambda_2) c_j \qquad (12)$$

$$I_d(\lambda_1)/I_0(\lambda_1) = D_s(\lambda_1) \cdot \exp(-\Sigma \mu(j, \lambda_1) L_{Aj}) \qquad (13)$$

$$I_d(\lambda_2)/I_0(\lambda_2) = D_s(\lambda_2) \cdot \exp(-\Sigma \mu(j, \lambda_2) L_{Aj}) \qquad (14)$$

In the case of a tissue of a human body used as an object, for example, the absolute value of the difference between the wavelengths $\lambda_1$ and $\lambda_2$ ($|\lambda_1 - \lambda_2|$) is at least 100 nm. For an absolute value of 30 nm or smaller, in particular, Equation (15) below expressing approximation holds true.

$$D_s(\lambda_1) \doteq D_s(\lambda_2) \qquad (15)$$

Equation (16) is obtained by elimination of $D_s$ from Equations (13) and (14) and application of Equation (15).

$$(I_d(\lambda_1)/I_d(\lambda_2))(I_0(\lambda_2)/I_0(\lambda_1))=\exp(-\Sigma(\mu(j,\lambda_1)-\mu(j,\lambda_2))L_{Aj})) \quad (16)$$

Let us now define the following equation:

$$x(j,\lambda_1,\lambda_2)=\mu(j,\lambda_1)-\mu(j,\lambda_2)=(\epsilon(\lambda_1)-\epsilon(\lambda_2))c_1 \quad (17)$$

Taking the natural logarithm ($\mathrm{Log}_e$) of both the sides of Equation (16) yields Equation (18) as follows:

$$-\mathrm{Log}_e((I_d(\lambda_1)/I_d(\lambda_2))(I_0(\lambda_2)/I_0(\lambda_1)))=\Sigma(x(j,\lambda_1,\lambda_2)L_{Aj}) \quad (18)$$

where $X(j, \lambda_1, \lambda_2)$ represents the right-hand side of Equation (17). Further, let y represent the following:

$$y=-\mathrm{Log}_e((I_d(\lambda_1)/I_d(\lambda_2))(I_0(\lambda_2)/I_0(\lambda_1))) \quad (19)$$

Equation (18) can then be rewritten into Equation (20) as follows:

$$y=\Sigma(x(j,\lambda_1,\lambda_2)L_{Aj}) \quad (20)$$

where $\Sigma$ used in Equation (20) denotes summation carried out for j=1 to n.

Figure 5:
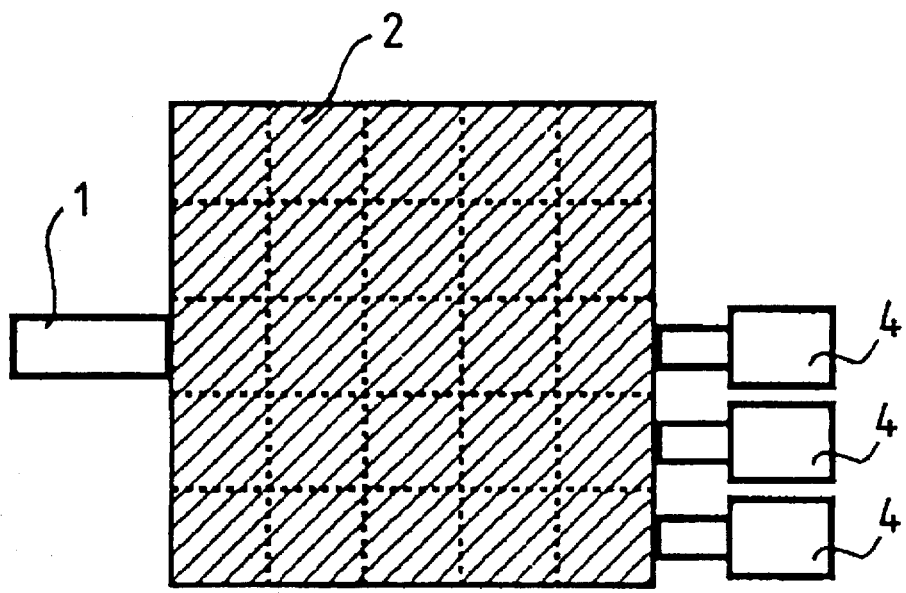
FIG. 5 is a diagram showing a typical layout of a light source and detectors in an object in accordance with the present invention.

Equation (20) is a linear equation. Unknown quantities $X(j, \lambda_1, \lambda_2)$ (j=1 to n) can be found from at least n lines of Equation (20). Each equation holds true for a measurement-position set, that is, a positional relation between the light source 1 and the detector 4, for an object. In order to provide n lines of Equation (20), one source light 1 and a plurality of detectors 4 placed at a plurality of detection positions on the object 2 are thus employed as shown in FIG. 5, or light is radiated from a plurality of incident positions and detected at n detection positions. The n lines of Equation (20) for the unknown quantities $X(j, \lambda_1, \lambda_2)$ (j=1 to n) and as many simultaneous equations as the unknown quantities are expressed by Equation (21).

$$y_1 = \Sigma(x(j,\lambda_1, \lambda_2)L_{A1j}) \quad (21)$$
$$\ldots$$
$$y_i = \Sigma(x(j,\lambda_1, \lambda_2)L_{Aij})$$
$$\ldots$$
$$y_n = \Sigma(x(j,\lambda_1, \lambda_2)L_{Anj})$$

where i is a subscript denoting the ith measurement-position set. It should be noted that FIG. 5 shows an example of a two-dimensional object.

Now, a measurement matrix Y, a matrix A expressing a spatial distribution of averaged photon-path lengths and an unknown matrix X comprising unknown quantities, are defined by Equations (22), (23) and (24) respectively.

$$Y=|y_1 \ldots y_i \ldots y_n|_T \quad (22)$$

where T means transposition and Y is a matrix comprising n rows and 1 column.

$$A=|L_{Aij}| \quad (23)$$

where A is a matrix comprising n rows and n columns and $L_{Aij}$ is an element of the matrix on the ith row and jth column $$X=|x(1,\lambda_1,\lambda_2) \ldots x(j,\lambda_1,\lambda_2) \ldots x(n,\lambda_1,\lambda_2)|T \quad (24)$$

where T means transposition and Y is a matrix comprising n rows and 1 column

The matrices Y, A and X are used to rewrite the simultaneous equations (21) into Equation (25).

$$Y=AX \quad (25)$$

In order to find the unknown matrix A from Equation (25), both the sides of Equation (25) are multiplied by the inverse matrix A(−1) of the unknown matrix A as shown in Equation (26)

$$A^{-1}Y=A^{-1}AX=X \quad (26)$$

Here, each element of the unknown matrix X found in this way is expressed by Equation (27) as follows:

$$x(j,\lambda_1,\lambda_2)=\mu(j,\lambda_1)-\mu(j,\lambda_2)=(\epsilon(\lambda_1)-\epsilon(\lambda_2))c_j \quad (27)$$

By substituting absorption coefficients for the wavelengths $\lambda_1$ and $\lambda_2$ of the incident lights into Equation (27), the absorber concentration $c_j$ for each volume element can be obtained.

In the above description, the object 2 is divided into n volume elements and lights are detected for n measurement-position sets through the use of n pairs of source lights 1 (incident positions) and detectors 4 to give simultaneous equations comprising n lines of Equation (20). By replacing n' with n which is equal to or greater than n (n'≥n), that is, by detecting light for n' measurement-position sets through the use of n' pairs of sources light 1 (incident positions) and detectors 4 to give simultaneous equations comprising n' lines of Eq(20), the unknown matrix X can be obtained in a way described below. Equations (22) and (23) described above are replaced with Equations (28) and (29) respectively as follows.

$$Y=|y_1 \ldots y_i \ldots y_{n'}|_T \quad (28)$$

where T means transposition and Y is a matrix comprising n' rows and 1 column.

$$A=|L_{Aij}| \quad (29)$$

where A is a matrix comprising n' rows and n columns and $L_{Aij}$ is an element of the matrix on the ith row and jth column. In general, a solution to Equation (25) with the matrices Y and A replaced as described above is given as follows:

$$X=((A_T)WA)^{-1}((A_T)W)Y \quad (30)$$

where T means transposition, At is the transposed matrix of the matrix A and W is a weight matrix comprising n' rows and n' columns. By using a unit matrix comprising n' rows and n' columns like the weight matrix W, Equation (30) can be rewritten into Equation (31):

$$X=((A_T)A)^{-1}(A_T)Y \quad (31)$$

As described above, by dividing the object 2 into n volume elements and by detecting light for n' measurement-position sets, where n' is greater than n (n'≥n), through the use of n' pairs of source lights 1 (incident positions) and detectors 4, the unknown matrix X, that is, the absorber concentrations $c_j$ in volume elements of an object, can be obtained with a high degree of accuracy.

In addition, according to the description given above, in the case of an object to be measured which object contains a multi-component absorber, concentrations of the multi-component absorber can be found by increasing the number of wavelengths of the incident light. For example, let the object contain two types of absorber: α and β. In this case, Equation (32), an extension of Equation (5) holds true.

$$I_d/I_0=D_s \cdot \exp(-(\epsilon_\alpha c_\alpha+\epsilon_\beta c_\beta)L_A) \quad (32)$$

where $\epsilon\alpha$, $\epsilon\beta$, $C_\alpha$ and $C_\beta$ are the molecular extinction coefficients and concentrations of the absorbers and α and β respectively. In the case of an object 2 divided into n volume elements as shown in FIG. 4, Equation (33) can be derived from Equation (32) as is the case with a single absorber type.

$$I_d/I_0 = D_s \cdot \exp\{-\epsilon_\alpha[c_{\alpha1}L_{A1}+\ldots+c_{\alpha n}L_{An}]+ \qquad (33)$$
$$\epsilon_\beta[c_{\beta1}L_{A1}+\ldots+c_{\beta n}L_{An}]\}$$
$$= D_s \cdot \exp\{-\Sigma(\epsilon_\alpha c_{\alpha j}+\epsilon_\beta c_{\beta j})L_{Aj}\}$$

where $\Sigma$ denotes summation carried out for j=1 to n.

Likewise, the attenuation constant $D_s$ can be eliminated from two equations for two incident lights with wavelengths $\lambda_1$ and $\lambda_2$ to give Equation (34).

$$(I_d(\lambda_1)/I_d(\lambda_2))(I_0(\lambda_2)/I_0(\lambda_1)) = \qquad (34)$$
$$\exp\{-\Sigma[(\epsilon_\alpha(\lambda_1)-\epsilon_\alpha(\lambda_2))c_{\alpha j}+(\epsilon_\beta(\lambda_1)-\epsilon_\beta(\lambda_2))c_{\beta j}]L_{Aj}\}$$

Similarly, let us define the following equation:

$$x(j,\lambda_1,\lambda_2)=(\epsilon_\alpha(\lambda_1)-\epsilon_\alpha(\lambda_2))c_{\alpha j}+(\epsilon_\beta(\lambda_1)-\epsilon_\beta(\lambda_2))c_{\beta j}) \qquad (35)$$

Equation (34) can then be rewritten into Equation (36) as follows:

$$(I_d(\lambda_1)/I_d(\lambda_2))(I_0(\lambda_2)/I_0(\lambda_1))=\exp\{-\Sigma x(j,\lambda_1,\lambda_2)L_{Aj}\} \qquad (36)$$

where $X(j, \lambda_1, \lambda_2)$ represents the right-hand side of Equation (35).

Likewise, an equation similar to Equation (36) can be obtained by elimination of $D_s$ from two equations for two incident lights with wavelengths $\lambda_1$ and $\lambda_3$.

$\Sigma$ in Equations (34) and (36) denotes summation carried out for j=1 to n. By taking the natural logarithm ($\text{Log}_e$) of both the sides of Equation (36), the equation becomes linear. Much like the case of a single type of an existing absorber explained earlier, light can then hereafter be detected for n' measurement-position sets where n' greater than n (n'≧n), through the use of n' pairs of source lights 1 (incident positions) and detectors 4, in order to solve Equation (36). In this way, the quantity $X(j, \lambda_1, \lambda_2)$ can thus be found. The quantity $X((j, \lambda_1, \lambda_3)$, a function of $\lambda_1$ and $\lambda_3$, and the quantity $X(j, \lambda_1, \lambda_2)$, a function of $\lambda_1$ and $\lambda_3$, are defined by simultaneous equations (37) as follows:

$$x(j,\lambda_1,\lambda_2)=(\epsilon_\alpha(\lambda_1)-\epsilon_\alpha(\lambda_2))c_{\alpha j}+(\epsilon\beta(\lambda_1)-\epsilon_{\beta2}(\lambda_2))c_{\beta j}x(j,\lambda_1,\lambda_3)=$$
$$(\epsilon_\alpha(\lambda_1)-\epsilon_\alpha(\lambda_3))c_{\alpha j}+(\epsilon_\beta(\lambda_1)-\epsilon_\beta(\lambda_3))c_{\beta j}) \qquad (37)$$

In the absorption coefficients of α and β, the two types of absorber, are known, their concentrations $c_\alpha$ and $c_\beta$ can be found for each volume element by substituting the absorption coefficients into Equation (37). In the case of γ types of absorbers existing in the object, the concentration distribution of each absorber can thus be found in a similar way by utilizing (γ+1) incident lights which have wavelengths different from each other.

It is needless to say that the techniques explained so far, which techniques are applicable to an object divided into a plurality of volume elements, can also be applied to an object not divided into volume elements by setting n, the number of volume elements, to unity (n=1). In the latter case, the left-hand side of Equation (29) is a matrix comprising n' rows and 1 column. The concentrations of the absorber can be found from the measurement matrix comprising n' measurement values measured for pairs of incident and detection positions arranged at a variety of locations in different directions and averaged photon-path lengths for the pairs. Of course, Equation (37) can also be applied even to the case of an object comprising a plurality of absorbers by not dividing the object into volume elements or by setting n, the number of volume elements, at unity (n=1). The value of an absorber concentration found in the ways described above is an averaged value in either a two-dimensional space or a three-dimensional space of the absorber. The averaged value in the former space is obtained by arranging the pairs of incident and detection positions on the circumference of a specific cross-sectional area of the object. The averaged value in the latter space is, on the other hand, obtained by arranging the pairs of incident and detection positions three-dimensionally around the object.

Figure 6:
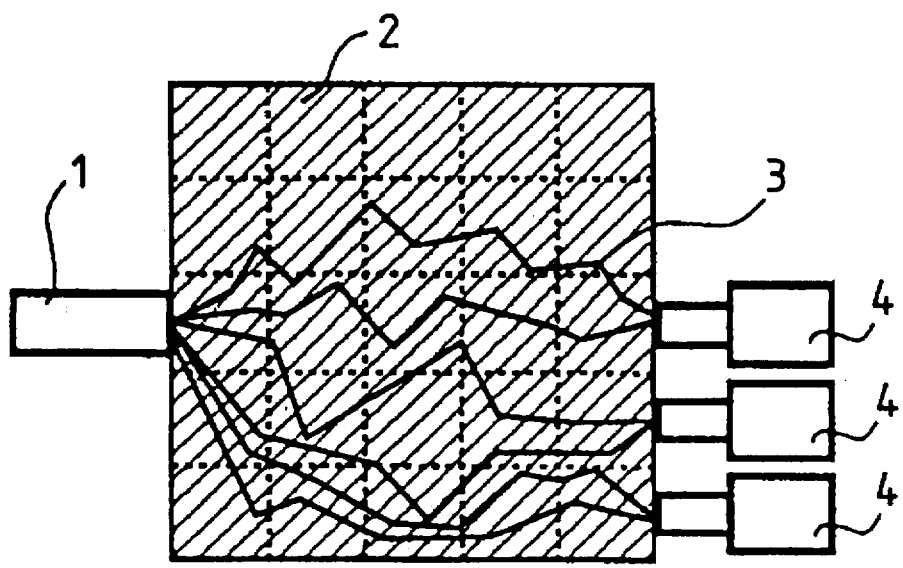
FIG. 6 is a diagram showing photon paths of photons arriving at detectors in a typical configuration provided by the present invention.

According to the description given so far, the values of the matrix A must be known in order to find the values of the matrix X. The element $L_{Aij}$ composing the matrix A is an averaged photon-path length in a jth volume element for an ith measurement-position set which represents a positional relation between the light source and a detector. That is to say, the value of an element $L_{Aij}$ can be found if the photon path arriving at the detector is known for each measurement-position set. FIG. 6 is a diagram showing a two-dimensional model for photon paths 3 of photons arriving at detectors 4 from a light source 1 through an object 2 in a typical configuration.

In the present invention, a simulation technique based on the Monte Carlo method for simulating the scattering of light in an object is adopted as a technique for finding a plurality of photon paths of photons arriving at detectors. A typical simulation technique based on the Monte Carlo method for simulating the scattering of light in an object, which technique is described in "A Monte Carlo Model for the Absorption and Flux Distributions of Light in Tissue," an article written by B. C. Wilson et al. in Med. Phys. 10(6), pages 824–830 (1983), is known. An overview of the Monte Carlo method adopted in the present invention, a well known method, is described as follows. A path traced by a photon originating from a light source is expressed in terms of polar coordinates (r, ø, θ) which are used to represent scattering points. The values of coordinates r, ø and θ of a subsequent point reached next by a photon leaving a present scattering point are found by stochastic prediction. The distance from the present scattering point to the next scattering point is found from a scattering length $L_s$ whereas an angular direction for determining the onward-movement direction of the photon is found from a scattering angle $\theta_s$ in the θ direction and a scattering angle $\phi_s$ in the ø direction. It should be noted that the substance, through which photons pass through, does not contain an absorber. The scattering length of a scattering phenomenon is expressed by Equation (38) as follows:

$$L_s=-(\log_e(R))/\mu_s \qquad (38)$$

where $\mu_s$ is a scattering coefficient and R is a uniform random number having values in the range 0 to 1 (0<R<1). The scattering angle $\theta_s$ in the θ direction can be expressed by Equation (39), which is derived from Heney-Greenstein 's equation, an approximation equation of a phase function obtained as an approximation typically from the Mie scattering theory, as follows.

$$\theta_s=\cos^{-1}[\{(1+g^2)-(1+g^2)^2/(1-g+2gR)^2\}/(2g)] \qquad (39)$$

where g is a cosine average of the phase function which shows an angular distribution of the scattering intensity in one scattering phenomenon and R is the uniform random number having values in the range 0 to 1 (0<R<1). It should be noted that the cosine average g can be expressed by the following equation:

$$g=(\int P_f \cos\theta d\omega)/(\int P_f d\omega)$$

where $P_f$ is the phase function and $\int$ denotes integration carried out over the solid-angle range ω=0 to 4 π. For general human-body substances, the cosine average g is known to have a value of about 0.9. In particular, for g=0, the scattering phenomenon is isotropic scattering, in which case, Equation (39) can be reduced to Equation (40) as follows:

$$\theta_s = \cos^{-1}(2R-1) \quad (40)$$

Since the scattering angle $\phi_s$ in the θ direction can be regarded as a quantity of a uniform probability distribution, Equation (40) can be further simplified to Equation (41) as follows:

$$\phi_s = 2R \quad (41)$$

where R is the uniform random number described earlier. Scattering points traced by a photon one after another can be expressed as a sequence of polar coordinates $(L_s, \theta_s, \phi_s)$ which can be found by stochastic prediction using the uniform random number R with values in the range 0 to 1 (0<R<1). The description of an overview of the Monte Carlo method adopted by the present invention is completed here.

When finding a photon path for an ith measurement-position set by simulation of a path traced by a photon using the Monte Carlo method, p(i, j) is used to represent a photon-path length in a jth volume element. As described earlier, by a measurement-position set, a combination of an incident position (or a light source) and a detection position is meant. m photon paths are calculated by simulation based on the Monte Carlo method described above and stored in memory. It should be noted that the number of photon paths must be high enough for allowing the light propagation through an actual object to be substantially reproduced. Even though the number of photon paths depends on the shape of the object, it is normally set at a value in the order of 1,000. The value of p(i, j) is then found for each photon path. L$Aij$ can be calculated by using Equation (42):

$$L_{Aij} = (\Sigma p(i,j,k))/m \quad (42)$$

where p(i, j, k) is p(i, j) for the kth photon path where k=1 to m and Σ denotes summation carried out for k=1 to m. By calculating $L_{Aij}$ for all measurement-point sets (i) and all volume elements (j), the matrix A expressing a spatial distribution of averaged photon-path lengths can then be found.

The procedure of the present invention described above applies to a case in which continuous light is used as an incident light and the intensity of the light passing through an object is used as a measurement signal. The procedure of the present invention described above is also applicable to a case in which pulsating light is used as an incident light and the total intensity representing the pulsating light passing through an object is used as a measurement signal. On top of that, a similar procedure can also be applied to a case in which the intensity of light passing through an object is measured by using a time-resolving technique and part of the measured light intensity is used as a measurement signal, allowing a distribution of the concentration of an absorber to be found.

Figure 7:
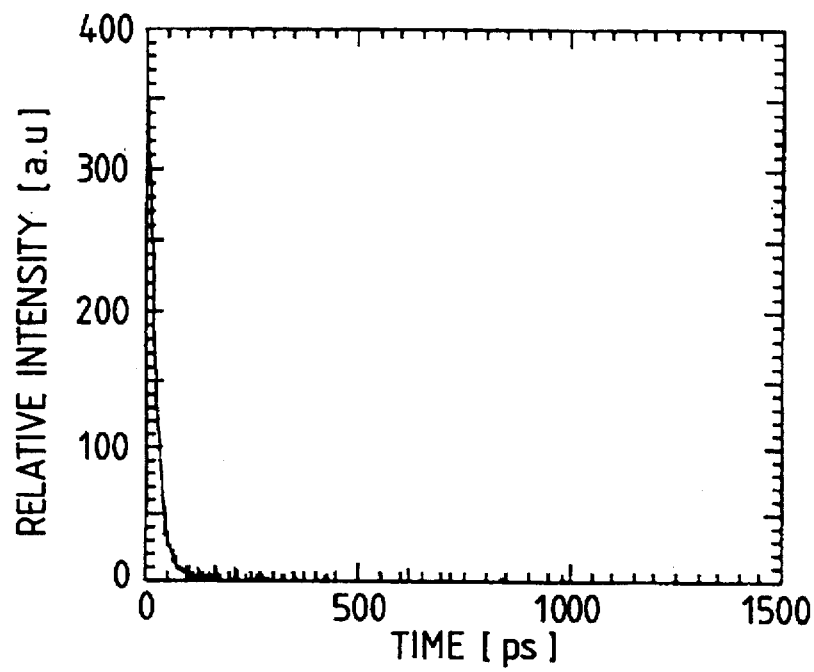
FIG. 7 is a diagram showing a typical temporal spectrum of an incident light which spectrum is used in a technique provided by the present invention.
Figure 8:
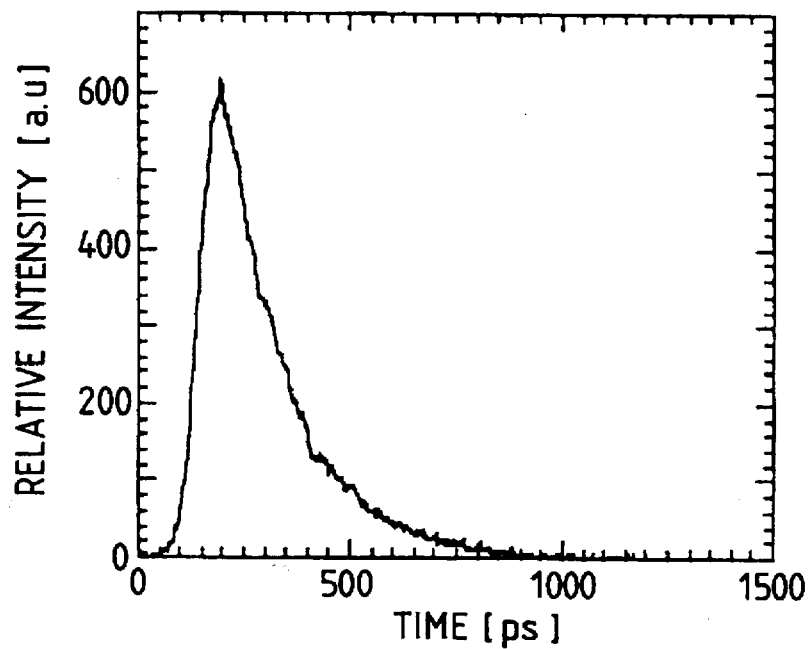
FIG. 8 is a diagram showing a typical temporal spectrum of a light detected after passing through an object which spectrum is used in a technique provided by the present invention.

A pulsating pulse with a shape resembling a δ function and having a temporal spectrum like the one shown in FIG. 7 is applied as an incident light to an object such as a predetermined portion of a human body. A time-resolving measurement of a transmitted intensity at a position on the other side facing the incident position by means of a streak camera results in a temporal spectrum $I_d(t)$ of the transmitted intensity which spreads in the time-axis direction as shown in FIG. 8. The horizontal axis of the figure represents a detection time, the lapse of time between the application of an incident pulsating light and the detection of the transmitted light. The reason why the temporal spectrum $I_d(t)$ of the detected intensity spreads in the time-axis direction is that, in the case of an object made of a scattering material, the detection time varies depending upon the photon-path length of the detected photon. In a system shown in FIG. 6, a temporal spectrum $I_{di}(t)$ of the detected intensity for an ith measurement-position set is measured. A detected intensity $I_{di}$ obtained by integration of the detected intensity $I_{di}(t)$ over a period between detection times $t_1$ and $t_2$ is used to find a measurement matrix Y. A matrix A expressing a spatial distribution of averaged photon-path lengths between the detection times $t_1$ and $t_2$ is then found. Finally, an unknown matrix X can be found by using the same procedure. The matrix A expressing a spatial distribution of averaged photon-path lengths between the detection times $t_1$ and $t_2$ can be found by calculation using Equation (42) for only photon paths of photons arriving at the detectors between the detection times $t_1$ and $t_2$. As described above, the temporal spectrum $I_{di}(t)$ is integrated over a time gate set between the detection times $t_1$ and $t_2$. By decreasing the width of the time gate, that is, the difference between the detection times $t_1$ and $t_2$ ($t_2-t_1$), the spatial resolution of the three-dimensional spatial distribution of the absorber concentration in the object to be eventually reconstructed and the quantitative accuracy of the procedure can be enhanced.

Figure 9:
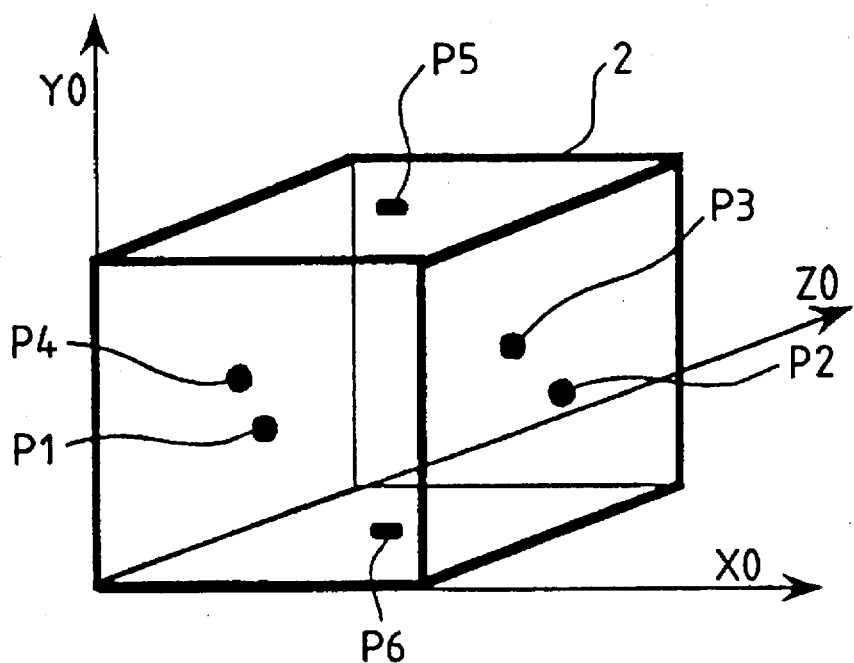
FIG. 9 is a diagram showing the shape of an object used in an embodiment provided by the present invention.

An embodiment actually adopting the technique described above is explained in detail as follows. First of all, for the sake of simplicity, an example in which the present invention is applied to a solid object simulating scattering characteristics of a human body is described. It should be noted, however, that the scope of the present invention is not limited to objects having solid-body shapes. It is needless to say that the present invention can also be applied to objects with any shapes as well. In the case of an object having an arbitrary shape, the shape of the object can be expressed approximately as an aggregation of small solid bodies. As an alternative, the internal portion of the object is expressed approximately as an aggregate of small bodies whereas portions including the outer surfaces of the object is expressed approximately as a small body which is partially defective. Furthermore, a space of a specific unit of a body to be inspected such as a spatial portion including a specific tissue part or a spatial portion including a tumor on a surface of a human body or at a location in close proximity to the surface can be expressed as an object member using the same technique described above. FIG. 9 is a diagram showing the shape of an object used in the embodiment. An object 2 shown in the figure is a cube having a side length of 25 mm. A coordinate system (X0, Y0, Z0) for expressing a location inside the object is shown in FIG. 9. As shown in the figure, notations P1 to P6 denote the surfaces of the object 2. Here, P1 is the surface for Z0=0 mm, P2 is the surface for X0=25 mm, P3 is the surface for Z0=25 mm, P4 is the surface for X0=0 mm, P5 is the surface for Y0=25 mm and P6 is the surface for Y0=0 mm. The scattering characteristics of the object 2 include $\mu_s=1.0$ mm-1, a value close to that of a human body, and g=0 where $\mu_s$ is the scattering coefficient used in Equation (38) and g is the cosine average of the phase function used in Equation (39) as described earlier. That is to say, the angular distribution of the scattered intensity in a scattering phenomenon is uniform and isotropic.

Figure 10:
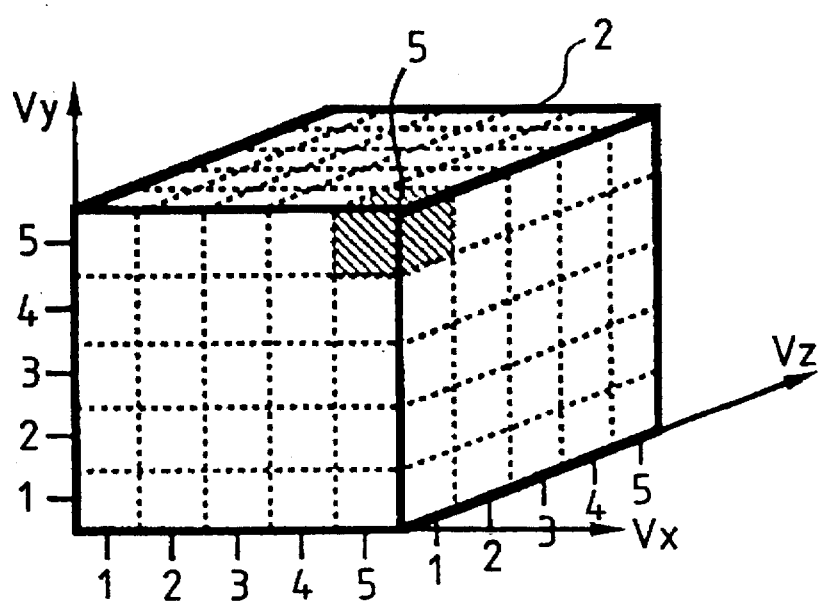
FIG. 10 is a diagram showing how an object used in an embodiment provided by the present invention is typically divided into volume elements.

In addition, the inside of the object 2 is divided into 5×5×5 model volume elements, the position of each of which is expressed as $(V_x, V_y, V_z)$ as shown in FIG. 10. A volume-element number j, a number assigned to each of the volume elements, is defined by Equation (43) as follows.

$$j = V_x + 5(V_y - 1) + 25(V_z - 1) \tag{43}$$

Figure 11:
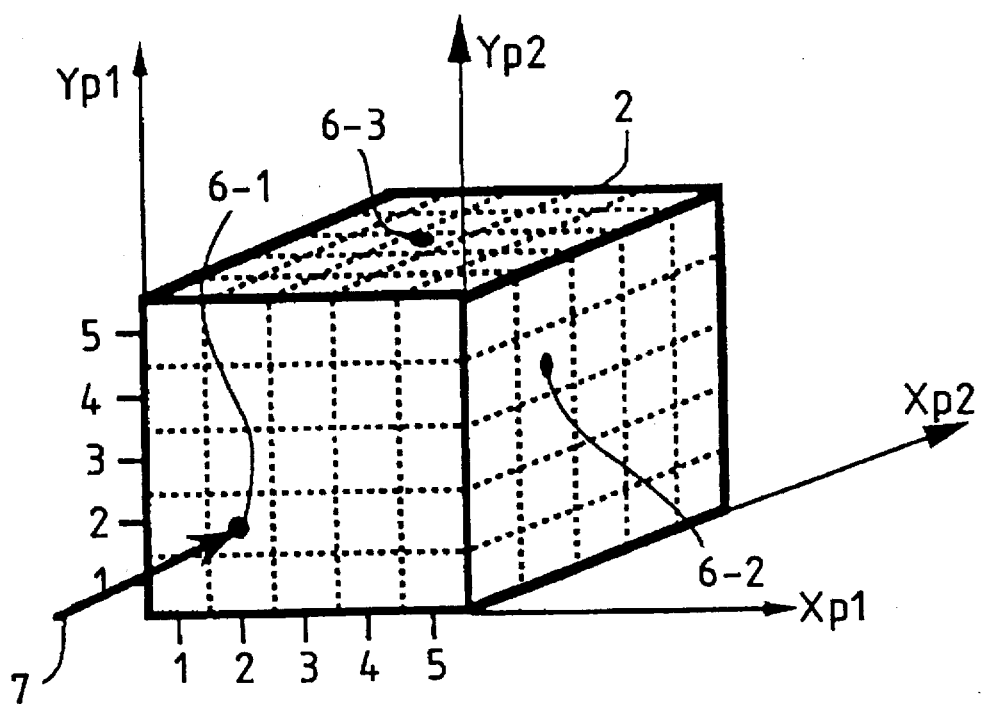
FIG. 11 is a diagram showing a typical layout of incident positions in an embodiment provided by the present invention.

For example, the position of a volume element 5 is (5, 5, 1) and the volume-element number j assigned to this volume element is 25 (j=25). FIG. 11 is a diagram showing the radiation of an incident light 7 from an incident position 6-1 on the surface P1 of the object shown in FIG. 8. In this embodiment, all incident and detection positions are each set at the location of the center of gravity on the surface of an arbitrary volume element coming in contact with a surface of the object. Coordinates $(X, Y)_{pi}$ pertaining to an ith surface Pi emitting light as shown in FIG. 9. are defined. By using these coordinates, incident positions 6-1, 6-2 and 6-3 are expressed as $(2, 2)_{p1}$, $(2, 2)_{p2}$ and $(3, 3)_{p5}$ respectively. Also in this embodiment, detection positions are placed on the centers of gravity of all volume-element surfaces on the object surfaces on the other side of the object facing the incident positions. As shown in FIG. 11, for example, for a light 7 radiated from an incident position 6-1 on the surface P1, detection positions are provided at 25 points on the surface P3 which faces the surface P1. At each of the detection positions, a detected intensity is measured. For definition of the surface Pi, refer to FIG. 9. In this embodiment, the object 2 is divided into a total of 125 volume elements. If the uniform absorber concentration in each of the volume elements is treated as an unknown quantity, there are 125 unknown quantities to be found. In order to find the 125 unknown quantities, as many measurement-position sets as the unknown quantities, that is, 125 measurement-position sets are also required as well. By a measurement-position set, a positional relation between a light source and a detector is meant. For this reason, 5 incident positions are provided at points $(2, 2)_{P1}$, $(2, 2)_{P2}$, $(4, 4)_{P3}$, $(4, 2)_{P4}$ and $(3, 3)_{P5}$ while detection positions are provided at 25 points on object surfaces facing object surfaces on which the incident positions are set to give a total of 125 measurement-position sets. For definition of the surface Pi, refer to FIG. 9.

Figure 12:
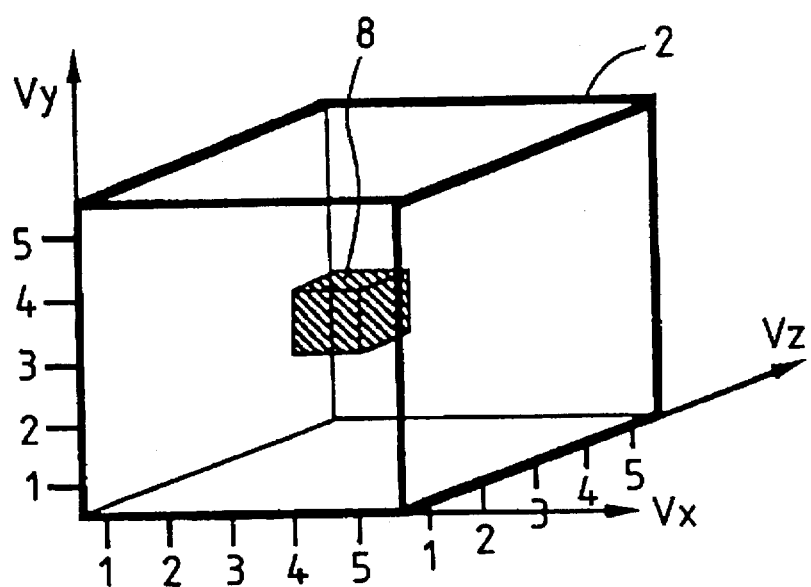
FIGS. 12 and 13 are diagrams showing positions of absorbers in objects used in embodiments provided by the present invention.
Figure 13:
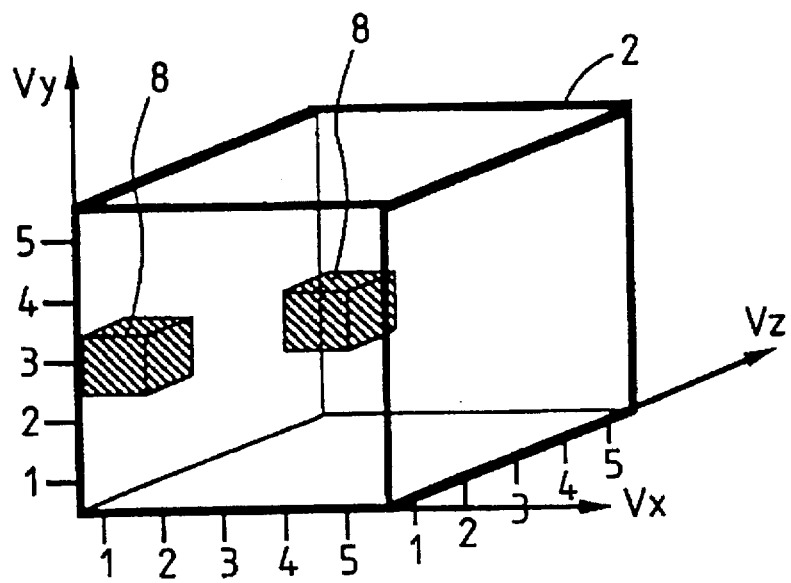

In this embodiment, two objects with absorber positions different from each other are used. The positions of absorbers inside the two objects are shown in FIGS. 12 and 13 respectively. Let the position of an absorber 8 in FIGS. 12 and 13 be represented by coordinates $(V_x, V_y, V_z)$. In the case of the object shown in FIG. 12, an absorber 8 having uniform concentration exists in a volume element at a location (3, 3, 3). In the case of the object shown in FIG. 13, on the other hand, two absorbers 8 each having uniform concentration exist in volume elements at locations (3, 3, 3) and (1, 3, 1) respectively. As incident lights, two pulsating lights having wavelengths $\lambda_1$ and $\lambda_2$ are used and transmitted intensities are measured at the detection positions using the time-resolving technique. The absorption coefficients of the absorbers at the wavelengths $\lambda_1$ and $\lambda_2$ are given as follows:

$$\epsilon(\lambda_1) = 1.0 \ [(\text{mm.mM})^{-1}] \text{ and } \epsilon(\lambda_2) = 0.0 \ [(\text{mm.mM})^{-1}]$$

whereas the absorber concentrations are all 0.01 [mM]. Typical temporal spectra $I_{di}(\lambda_1, t)$ and $I_{di}(\lambda_2, t)$ of the transmitted intensity (or the detected intensity) obtained by the Monte Carlo simulation explained earlier are shown in FIG. 14. The horizontal axis represents the detection time. As the origin of the horizontal axis, the time at which a photon arrives at a detection position directly without being scattered is taken. It should be noted that, much like FIGS. 7 and 8, the detection time can be multiplied by the velocity of the light in the medium through which the photon is traveling, allowing the horizontal axis to represent a distance traveled by a photon instead of the detection time. In this embodiment, values obtained by integration of the temporal spectra $I_{di}(\lambda_1, t)$ and $I_{di}(\lambda_2, t)$ of the detected intensity at an ith measurement-position set over a period from a detection time $t_1=0$ [ps] to a detection time $t_2=1,500$ [ps] are used as detected intensities $I_{di}(\lambda_1)$ and $I_{di}(\lambda_2)$ at the ith measurement-position set. It should be noted that, by setting the detection time $t_2$ at a value smaller than 1,500 [ps], the spatial resolution and the quantitative accuracy of the three-dimensional distribution of the absorber to be found eventually can be further improved.

Figure 15:
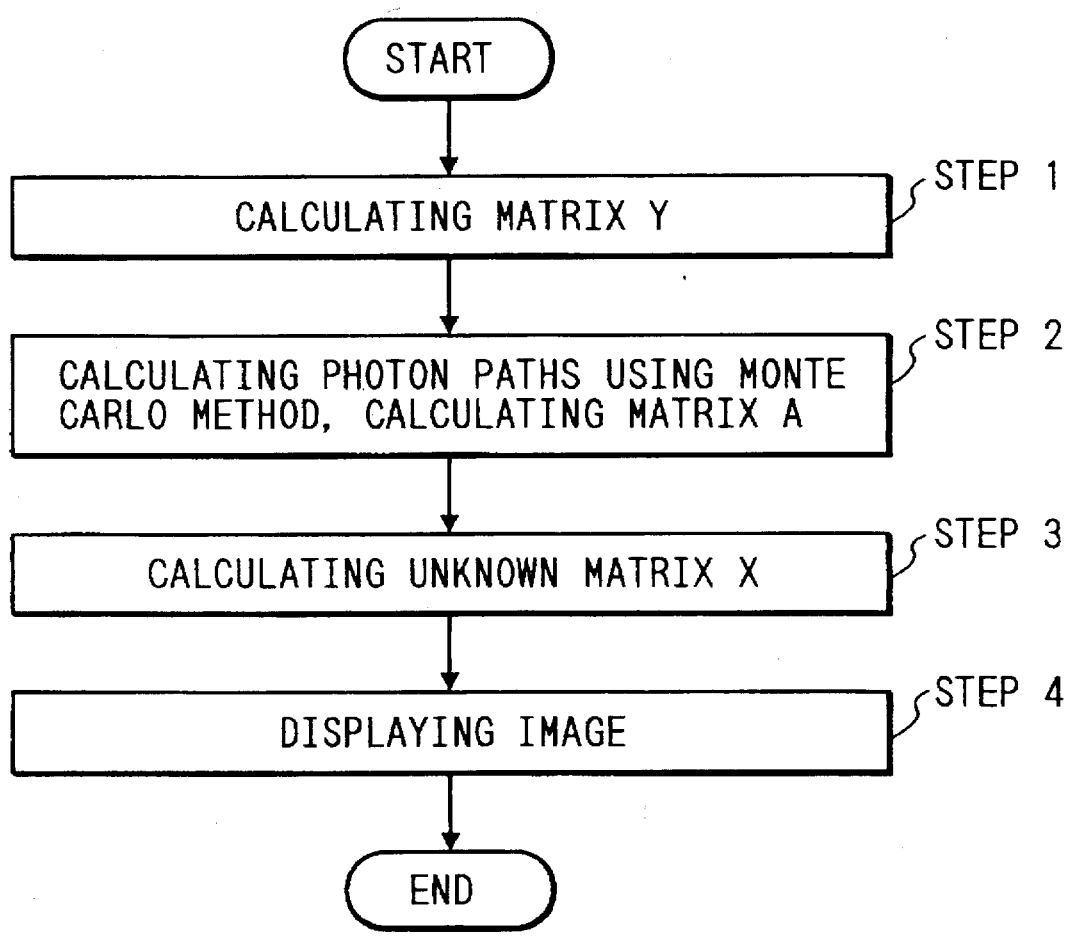
FIGS. 15, 16 and 17 show flowcharts of a procedure for finding a spatial distribution of the concentration of an absorber in an object which procedure is provided by the present invention.

FIG. 15 shows an outline of a flowchart of a procedure for producing an image of the concentration of an absorber existing in an object. The imaging procedure comprises the following four main steps: step 1 of creating a measurement matrix Y; step 2 of creating a matrix A expressing a spatial distribution of averaged photon-path lengths; step 3 of deriving an unknown matrix X from the matrix Y and the inverse matrix of the matrix A; and step 4 of finding absorber concentrations in an object from the derived unknown matrix X and displaying a spatial distribution of the absorber concentrations.

Figure 16:
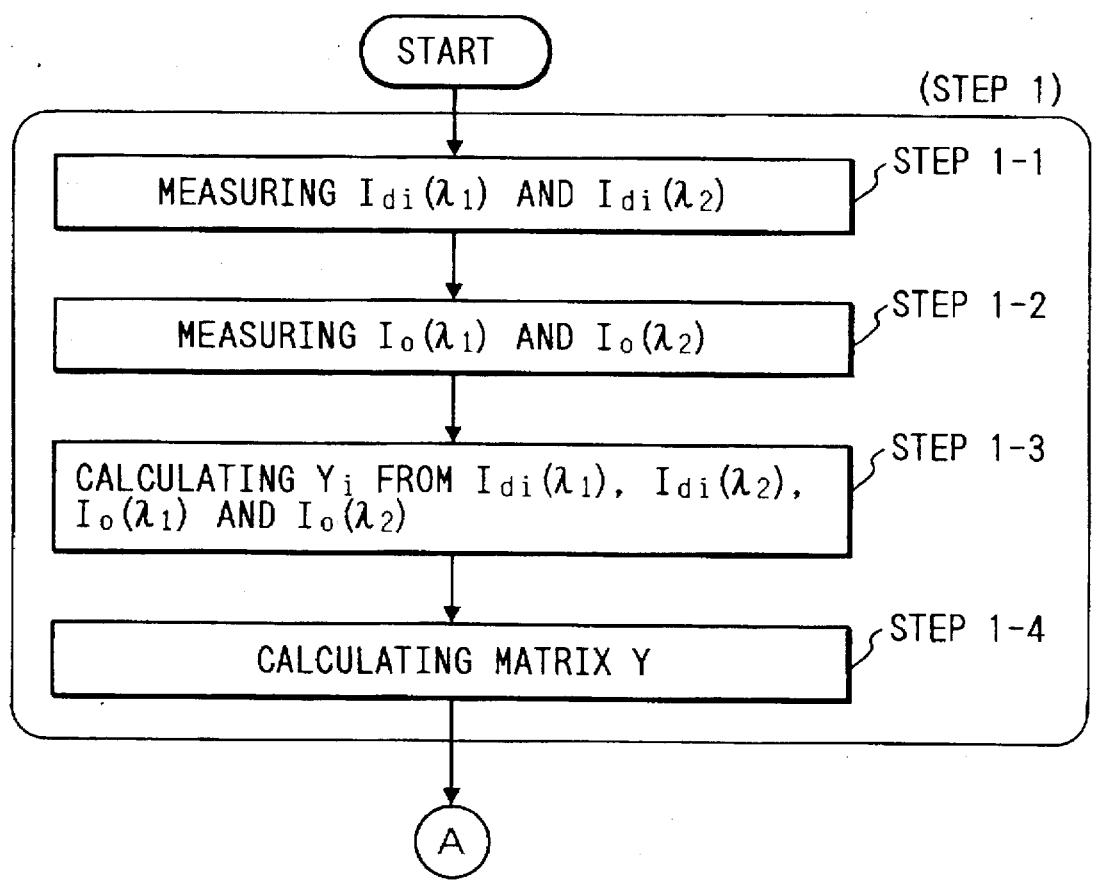

It should be noted that, in some cases, data paths have been calculated by using the Monte Carlo method prior to the start of the processing carried out at the step 2 and data-path data has been stored in a storage means. In such cases, it is needless to say that the stored photon-path data is used in creating the matrix A. A detailed procedure followed at each step is explained by referring to a flowchart shown FIGS. 16 and 17 as follows.

[step 1] Creation of Measurement Matrix Y step 1-1: Transmitted intensities are calculated for each measurement-position set and the detected intensities $I_{di}(\lambda_1)$ and $I_{di}(\lambda_2)$ are found.

step 1-2: Incident intensities $I_{d0}(\lambda_1)$ and $I_{d0}(\lambda_2)$ at two wavelengths are calculated using incident lights for each measurement-position set.

step 1-3: $y_i$ is obtained by substituting the detected intensities $I_{di}(\lambda_1)$, $I_{di}(\lambda_2)$, $I_{d0}(\lambda_1)$ and $I_{d0}(\lambda_2)$ calculated at the steps 1-1 and 1-2 into Equation (19) after completing calculations for all measurement-position sets.step 1-4: A measurement matrix Y is created with $y_i$ (i=1 to 125) obtained at the steps 1-3 used as elements thereof.

[step 2] Creation of Matrix A Expressing Spatial Distribution of Averaged Photon-Path Lengths step 2-1: The three-dimensional external shape of the object to be measured is measured and coordinate data representing the external shape is input to a processing unit in order to create model-object data. As a technique for measuring the external shape, a method such as the optical cutting process, the MRI (Magnetic Resonance Imaging) or X-ray CT can be adopted. In this embodiment, the object is a cube with a side length of 25 mm and its external-shape data is input.

step 2-2: Coordinate data of measurement-position sets (pairs of incident and detection positions) established at the measurement time is input. In this embodiment, coordinate data of 125 measurement-position sets described earlier is input to the processing unit.

step 2-3: The scattering coefficient $\mu_s$ of the absorber and the cosine average g of the phase function are input to the processing unit as scattering characteristics of the object of measurement. In this embodiment, the scattering coefficient μ=1.0 mm-1 and g=0, a quantity representing directivity, are used.

step 2-4: Calculation by simulation of scattering in the object containing no absorber is carried out using the Monte Carlo method which simulation is based on parameters input at the steps 2-1 to 2-3. At this step, a plurality of photon paths are calculated for each preset measurement-position set (i) and an averaged photon-path length $L_{Aij}$ for each volume element (j) and for each measurement-position set (i), that is, a spatial distribution of averaged photon-path lengths is stored in memory. In this case, if transmitted intensities are to be measured by using the time-resolving technique, the spatial distribution $L_{Aij}$ of averaged photon-path lengths is found to be stored in memory only from parameters for photon paths of photons arriving at detectors as measurement signals between detection times $t_1$ and $t_2$. In this embodiment, 30,000 photon paths are calculated for each measurement-position set and the detection period is between detection times 0 [psec] and 1,500 [psec]. An overview of the Monte Carlo method used at this step has been explained. It should be noted that photon paths may have been calculated and photon-path data may have been stored in memory prior to the start of the processing carried out at the step 2-4. In this case, it is needless to say that the photon-path data stored and preserved in the memory is used. A processing method for finding an averaged photon-path length $L_{Aij}$ for each volume element (j) and for each measurement-position set (i) will be explained in detail later for a case in which the photon-path data has been stored and preserved in memory.

step 2-5: A matrix A defined by Equation (23) for expressing a spatial distribution of averaged photon-path lengths is created with $L_{Aij}$ (i=1 to 125 and j=1 to 125) for all volume elements (j) and for all measurement-position sets (i), which have been found earlier, used as elements of the matrix. It should be noted, however, that if the shape of the object to be measured is known or if a known shape resembling the shape of the object is available for measurement use, the matrix A expressing a spatial distribution of averaged photon-path lengths is calculated in advance. When the object is the head or the breast of a human body, for example, matrices A each expressing a spatial distribution of averaged photon-path lengths are calculated in advance for a plurality of head-shape and breast-shape types. A matrix A expressing a spatial distribution of averaged photon-path lengths, which matrix has been calculated for a shape type most resembling the shape of the head or breast of a human body used as an actual object to be measured, is then selected. In addition, the head of a human body can be approximated as a sphere or an ellipsoid in the calculation.

[step 3] Derivation of Unknown Matrix X from Matrix Y and Inverse Matrix of Matrix A step 3-1: An unknown matrix X is found by substituting the measurement matrix Y created at the step 1-4 and an inverse matrix $A^{-1}$ found from the matrix A expressing a spatial distribution of averaged photon-path lengths created at the step 2-5 into Equation (26). Of course, the unknown matrix X can also be found from Equation (30).

step 3-2: An absorber concentration in each volume element is found by substituting absorption coefficients of the absorber for wavelengths of incident lights into Equation (27) which expresses each element of the unknown matrix X.

[step 4] Displaying Image of Spatial Distribution of Absorber Concentration

A distribution of absorber concentration on an arbitrary cross layer extracted from the spatial distribution of averaged photon-path lengths obtained at the step 3 is displayed as an image.

Figure 18:
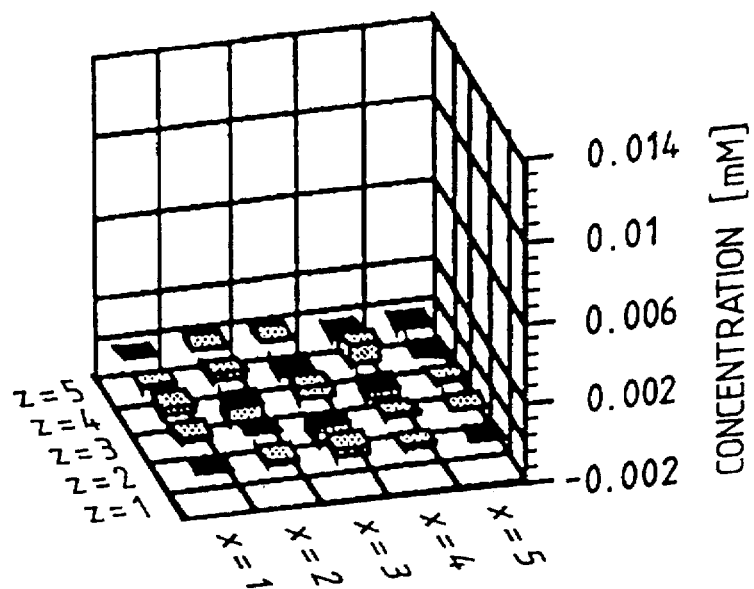
FIGS. 18 to 24 are diagrams showing typical spatial distributions of concentrations of absorbers found by the imaging technique provided by the present invention.
Figure 19:
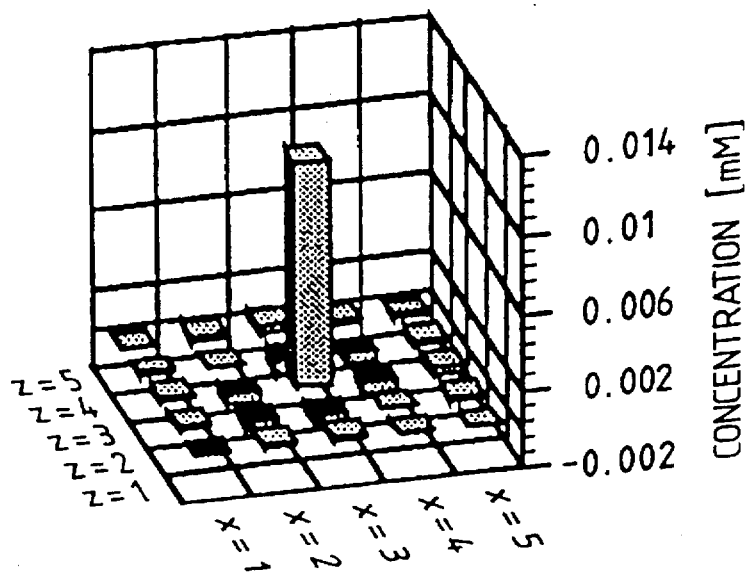
Figure 20:
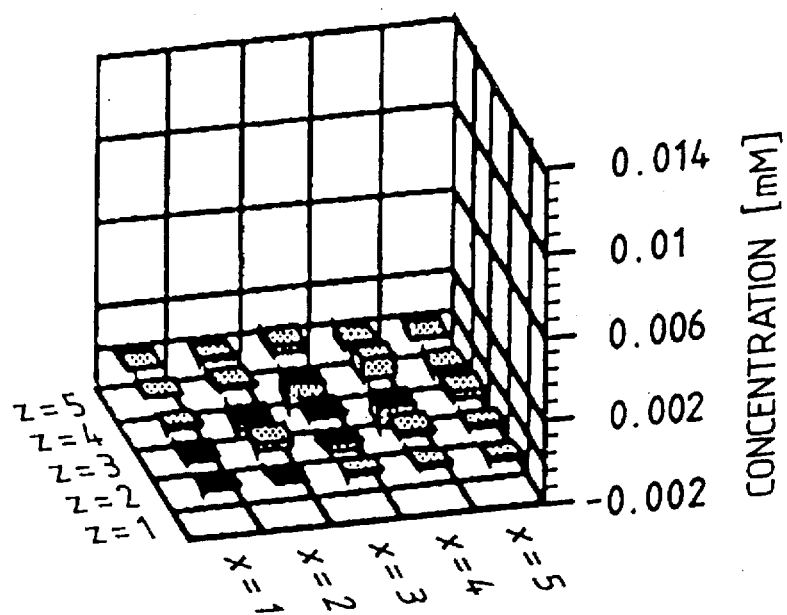
Figure 21:
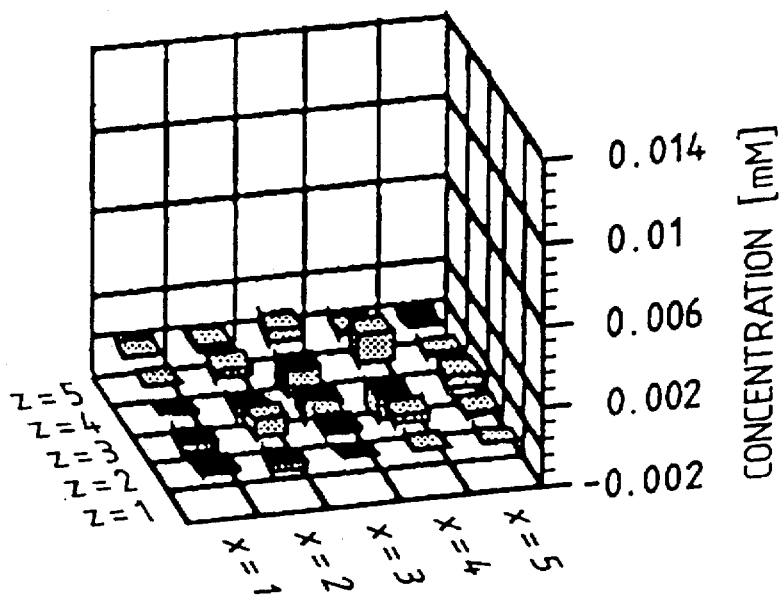
Figure 22:
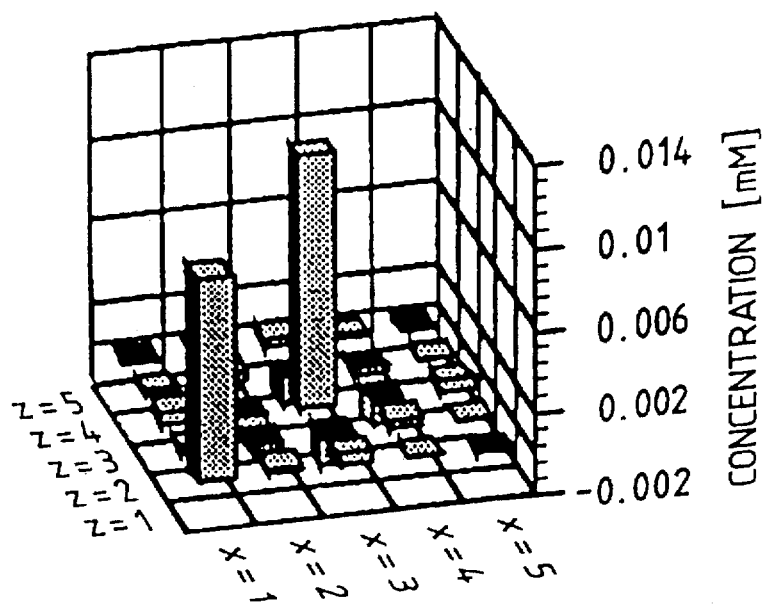
Figure 23:
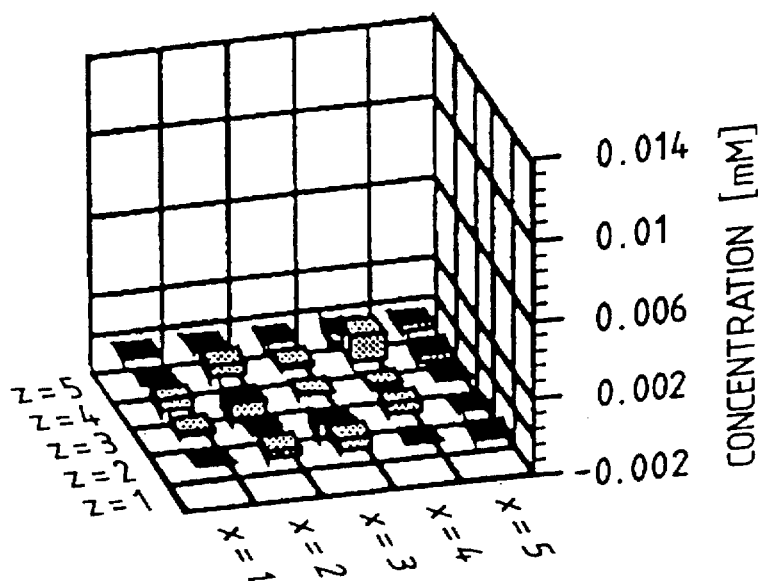

FIGS. 18 to 23 are diagrams showing data of spatial distributions of concentrations of absorbers found in accordance with the flowcharts described above. FIGS. 18 to 20 are diagrams showing data of spatial distributions of absorber concentrations in the object shown in FIG. 12. To be more specific, diagrams of FIGS. 18 to 20 show data for surfaces of $V_y=2$, $V_y=3$ and $V_y=4$ respectively. FIGS. 21 to 23 are, on the other hand, diagrams showing data of spatial distributions of absorber concentrations in the object shown in FIG. 13. To be more specific, diagrams of FIGS. 21 to 23 show data for surfaces of $V_y=2$, $V_y=3$ and $V_y=4$ respectively. In FIGS. 18 to 23, the numbers following the notations 'x=', 'y=' and 'z=' are values for the coordinates x, y and z respectively. In the above calculations, the scattering coefficient of the object is set at 1.0 mm-1 (μ=1.0), a value close to the scattering coefficient of a human body, and the cosine average g of the phase function used in Equation (39) is assumed to be zero (g=0), representing isotropic scattering. For an ordinary human body related substance, the cosine average g is known to have a value of about 0.9. In spite of the fact that g=0 is assumed in the above calculations, the obtained results clearly reproduce spatial distributions of absorber concentrations in the objects that has been set in advance. A space having dimensions of 5×5×5 and different absorber concentrations are clearly recognized and the spatial resolution is also excellent as well.

Figure 14:
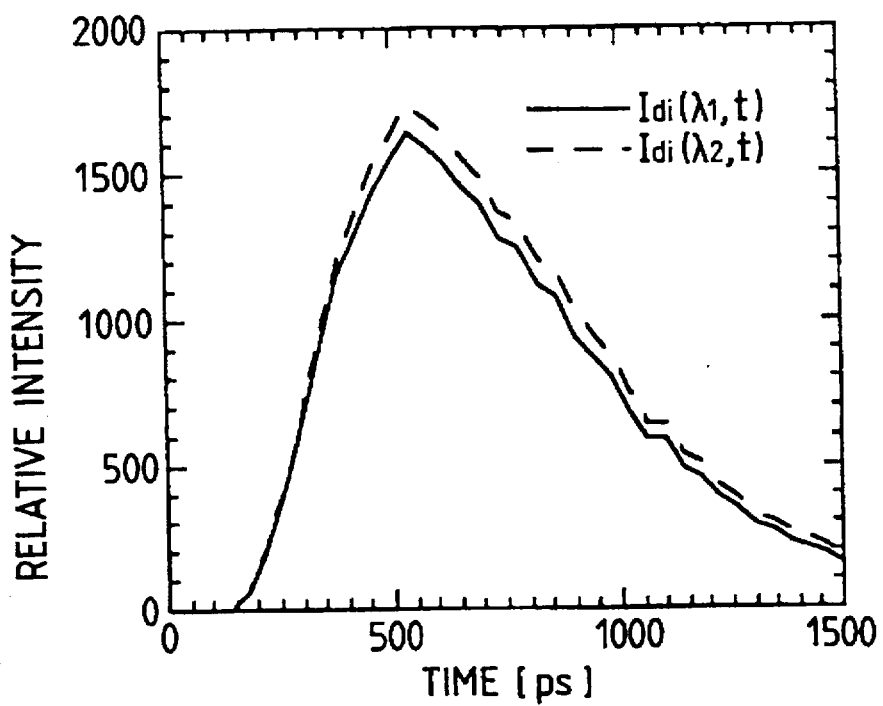
FIG. 14 is a diagram showing a typical temporal spectrum of a detected light found by calculation in accordance with the present invention.
Figure 24:
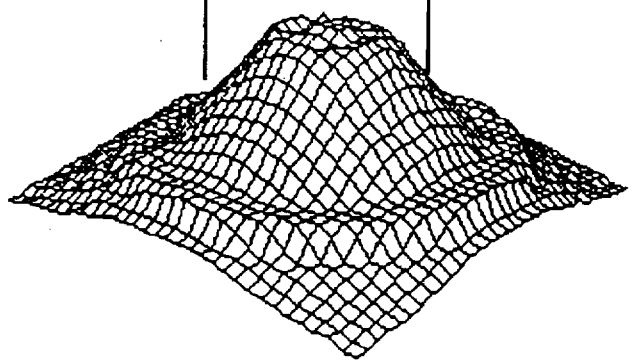

Typical data resulting from calculation using an algorithm of the X-ray CT called the Filtered Back Projection method is shown in FIG. 24. This figure shows a reconstructed image concerning an object wherein a cylindrical absorber having an external diameter of 5.00 mm and a height of 100 mm is placed along the center axis of a cylinder having an external diameter of 25 mm and a height of 100 mm. The cylindrical absorber is a perfect absorber which is often assumed in the evaluation of spatial resolution and has an infinite absorption coefficient. As measurement data used in the reconstruction of the image, a temporal spectrum of detected intensities like the one shown in FIG. 14 is generated by simulation using the Monte Carlo method, an overview of which has been described earlier, with incident light arriving at the object regarded as having a shape like a δ-function. In order to enhance the spatial resolution of the image, the width of the time gate is set at a reduced value and a signal resulting from integration of the temporal spectrum of the detected intensity over the period of time 0 [psec] to 300 [psec] is used as a measurement signal. A cross-layer image is found by calculation using the Filtered Back Projection method at the center position of the longitudinal direction of the cylinder.

FIG. 24 is a three-dimensional diagram showing the resulting reconstructed image. The image is displayed at a longitudinal-direction minimum interval of 0.05 with the maximum of values in the longitudinal direction set at 1.0. It is obvious from comparison of FIGS. 18 through 23 to FIG. 24 that the imaging method provided by the present invention clearly has spatial resolution better than that of the conventional technique. With the Filtered Back Projection method, effects of scattering can not be taken into consideration sufficiently, making it difficult to obtain high resolution due to an inevitably deteriorating S/N ratio even if a measurement signal obtained by integration of a temporal spectrum of the detected intensity over a shortened period of time is used. In the case of the result shown in FIG. 24, the spatial resolution is evaluated, at a full width half maximum, to be 15 mm for an absorber having an external diameter of 5 mm. In the case of the results shown in FIGS. 18 to 23 for the reconstruction of absorbers having dimensions of 5 mm×5 mm×5 mm, on the other hand, the absorbers are clearly detected with a high degree of sharpness. As such, the spatial resolution of the imaging method provided by the present invention is improved by about three times or more over the Filtered Back Projection method.

Figure 25:
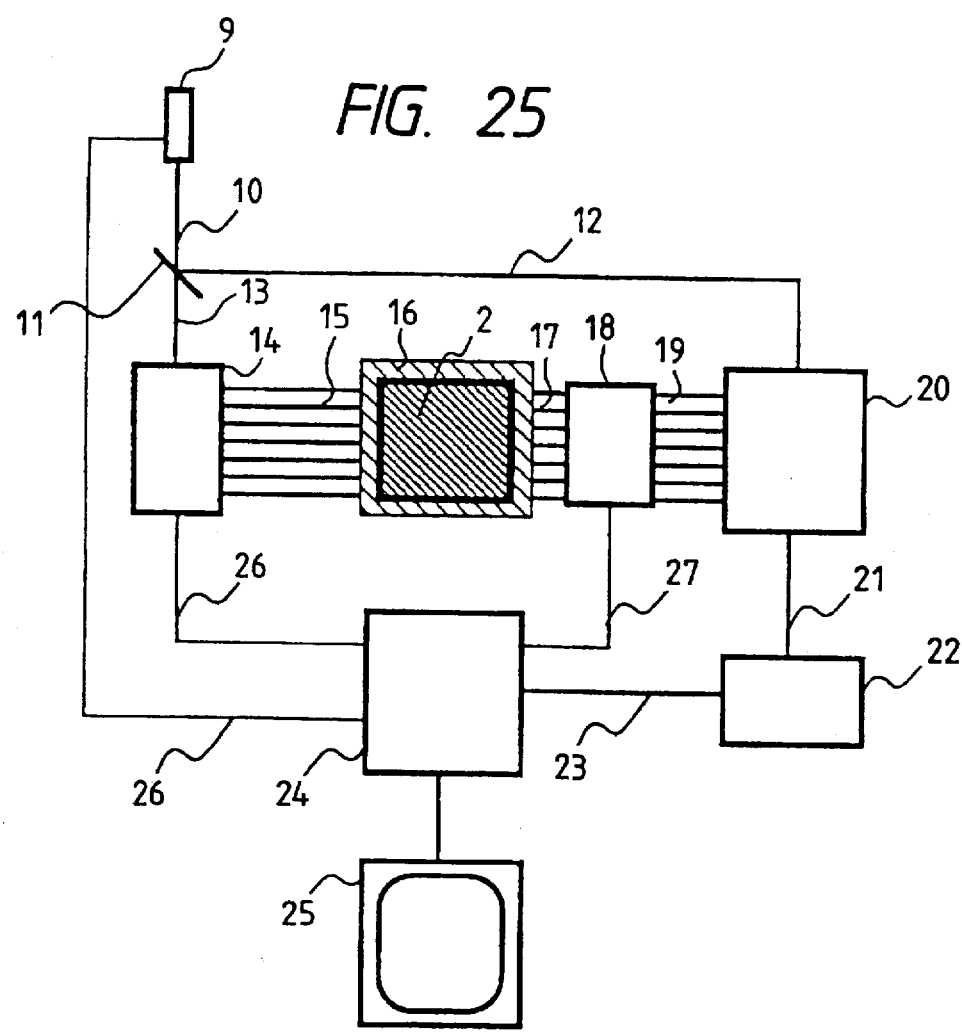
FIG. 25 is a diagram showing the configuration of a device adopting the technique provided by the present invention.

FIG. 25 is a diagram used for explaining the configuration of a device adopting the imaging technique provided by the present invention. A light source 9 generates light having at least two different wavelengths. Typically, the light source 9 is a Ti sapphire laser or comprises a plurality of semiconductor lasers. Switching from one wavelength to another is controlled by a computer 24. First of all, a light generated by the light source 9 at a first wavelength $\lambda_1$ is selected. After passing through a light-source waveguide 10 comprising, among other optical systems, optical fibers and lenses, the selected light is split by an optical directional coupler 11 into two beams traveling through two systems: a reference-light waveguide 12 and a light-source optical fiber 13. It should be noted that, unless specified otherwise, a waveguide can be assumed hereafter to be an optical fiber or to comprise optical systems. The split light traveling through the reference-light waveguide 12 is measured by an optical detector 20 such as a streak camera as a reference light having a radiated intensity $I_0$. The split light traveling through the light-source optical fiber 13, on the other hand, arrives at an optical switch 14 for selecting one out off a plurality of incident-light optical fibers 15 arranged on the surface of an object 2. The selected incident-light optical fiber 15 is connected to the light-source optical fiber 13 by the optical switch 14, allowing the light traveling through the light-source optical fiber 13 to be radiated to the inside of the object 2 from an arbitrary position on the object 2.

Here, the incident-light optical fibers 15 are securely fixed at their installation positions on the object 2 by an optical-fiber securing holder 16. The light passing through the object 2 enters a plurality of light-detection optical fibers 17 arranged on the surface of the object 2. An optical switch 18 is used for selecting only needed light-detection optical fibers 17 to be connected to the detector optical fibers 19. Lights which are to be detected after passing through the selected light-detection optical fibers 17 are lead to an optical detector 20 in which a time-resolved signal representing a detected intensity is measured for each connected detector optical fiber 19. The intensity signal of the light source and the time-resolved signal representing the detected intensity is transmitted through a signal transmitting line 21 to an A/D converter 22 for converting the intensity and time-resolved signals into digital ones. The digital signals representing the light-source and detected intensities are then transmitted through another signal transmitting line 23 to a computer 24 for storing the digital signals in a storage device employed therein.

Subsequently, a light having a wavelength $\lambda_2$ different from $\lambda_1$ is selected to undergo the same measurement process described above. As the measurement for an incident position is completed, measurement is started for another incident position or other detection positions selected by actuation of the switch 14 or 18 under the control of the computer 24 via a switch control line 26 or 27. The computer 24 changes the connection position between the light-source optical fiber 13 and the incident-light optical fibers 15 or the connection positions between the light-detection optical fibers 17 and the detector optical fibers 19. As the required measurements are completed, a spatial distribution of the absorber concentration is found to be displayed on a display unit 25 in accordance with the procedure indicated by the flowcharts shown in FIGS. 15, 16 and 17.

Figure 26:
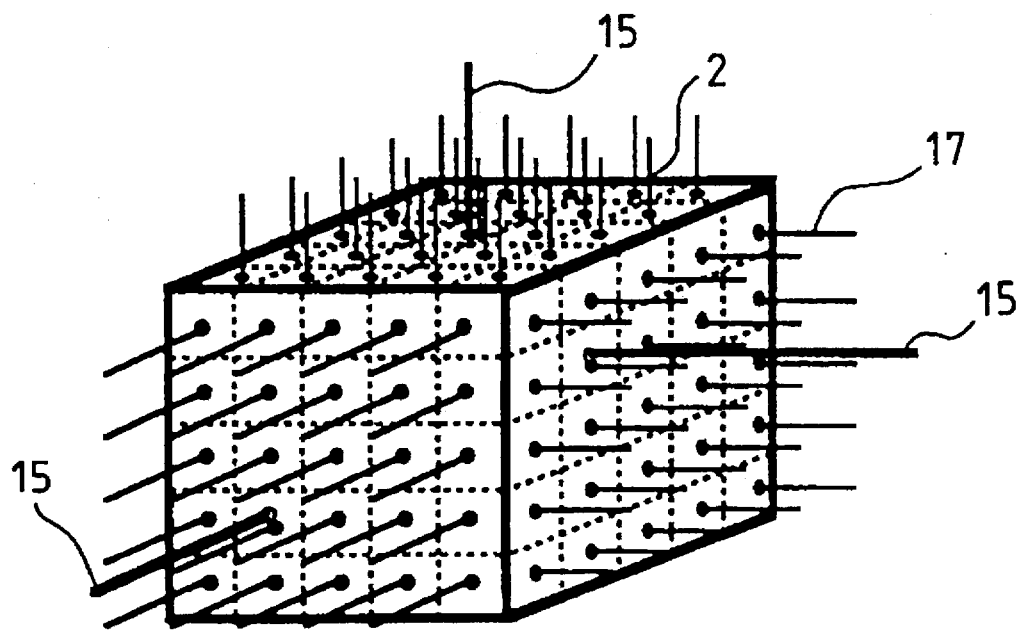
FIG. 26 is a diagram showing a typical arrangement of optical fibers for applying incident lights to an object and for detecting the lights which arrangement is made in accordance with the present invention.

FIG. 26 is a diagram showing a typical arrangement of incident light optical-fibers 15 and light-detection optical fibers 17. The notation Pi denoting a surface of the object is defined in the same way as that of FIG. 9. In order to make the same arrangement of incident and detection positions as that shown in FIG. 9, the incident-light optical fibers 15 are attached to five points $(2, 2)_{P1}$, $(2, 2)_{P2}$, $(4, 4)_{P3}$, $(4, 2)_{P4}$ and $(3, 3)_{P5}$. On the other hand, the light-detection optical fibers 17 are located at the centers of gravity of all volume-element surfaces on the surfaces P1 to P5. It should be noted that, at each of the five points, two fibers, that is, an incident-light optical fiber 15 and a light-detection optical fiber 17 are set. In this case, the two fibers 15 and 17 are attached to each of the points by slightly shifting their ends apart from each other. The incident-light optical fibers 15 and the light-detection optical fibers 17 are made of a quartz-fiber material with a typical diameter of 1 mm.

Figure 27:
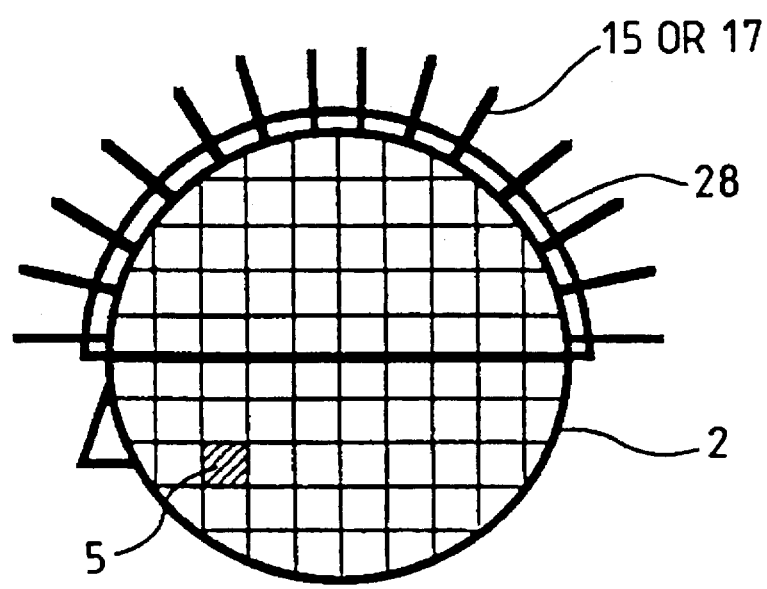
FIG. 27 is a diagram showing a typical arrangement of optical fibers for applying incident lights to the head of a human body and for detecting the lights which arrangement is made in accordance with the present invention.

FIG. 27 is a diagram showing a typical arrangement of incident-light optical fibers 15 and light-detection optical fibers 17 with the head of a human body used as the object 2. In the case of the head of a human body used as an object, a helmet-like optical-fiber fixing holder 28 is employed for securely holding the incident-light optical fibers 15 and light-detection optical fibers 17. The optical-fiber fixing holder 28 has holes for inserting the incident-light optical fibers 15 and light-detection optical fibers 17. Each fiber is inserted into an arbitrary hole. Even in the case of a human-body object, a model volume element 5 is generally a cube. As shown in FIG. 27, however, an model volume element 5 that comes in contact with the surface of the head is not a cube.

Here, let the object be divided into 1,000 volume elements. In this case, it is necessary to provide at least 1,000 measurement-position sets or relations between incident and detection positions. There are several ways to arrange the incident-light optical fibers 15 and light-detection optical fibers 17 shown in FIG. 25 in order to establish 1,000 measurement-position sets. For example, at least 20 incident-light optical fibers 15 and at least 1,000 light-detection optical fibers 17 are used. When lights are radiated from at least 20 incident-light optical fibers 15, at least 50 out off 1,000 light-detection optical fibers 17 are selected to measure detected intensities. This measurement can be implemented by a device configuration like the one shown in FIG. 25.

When a near-infrared light is used as an incident light applied to the head of a human body, the oxygenated hemoglobin referred to hereafter as $HbO_2$ and the deoxygenated hemoglobin referred to hereafter as Hb serve as dominating absorbers. It is possible to find spatial distributions of concentrations of these two components. In this case, light having three different wavelengths $\lambda_1$, $\lambda_2$ and $\lambda_3$ is used as incident beams. Optical measurements are carried out for each of the wavelengths. From the measurements using lights with the wavelenghts $\lambda_1$ and $\lambda_2$ as incident lights, an unknown matrix X comprising elements $X(j, \lambda_1, \lambda_2)$ is found in accordance with the steps 1 to 3 of the procedure shown as flowcharts in FIGS. 15 to 17. Then, from the measurements using lights with the wavelenghts $\lambda_1$ and $\lambda_3$ as incident lights, elements $X(j, \lambda_1, \lambda_3)$ are found in the same way. From the found elements $X(j, \lambda_1, \lambda_2)$ and $X(j, \lambda_1, \lambda_3)$, simultaneous equations (or Equation (37)) are established. The simultaneous equations (or Equation (37)) are solved by substituting absorption coefficients $\epsilon$ of the absorbers for the lights having the wavelengths thereto to find the concentration of Hb in each volume element c(Hb, j) and the concentration of $HbO_2$ in each volume element c($HbO_2$, j).

Figure 28:
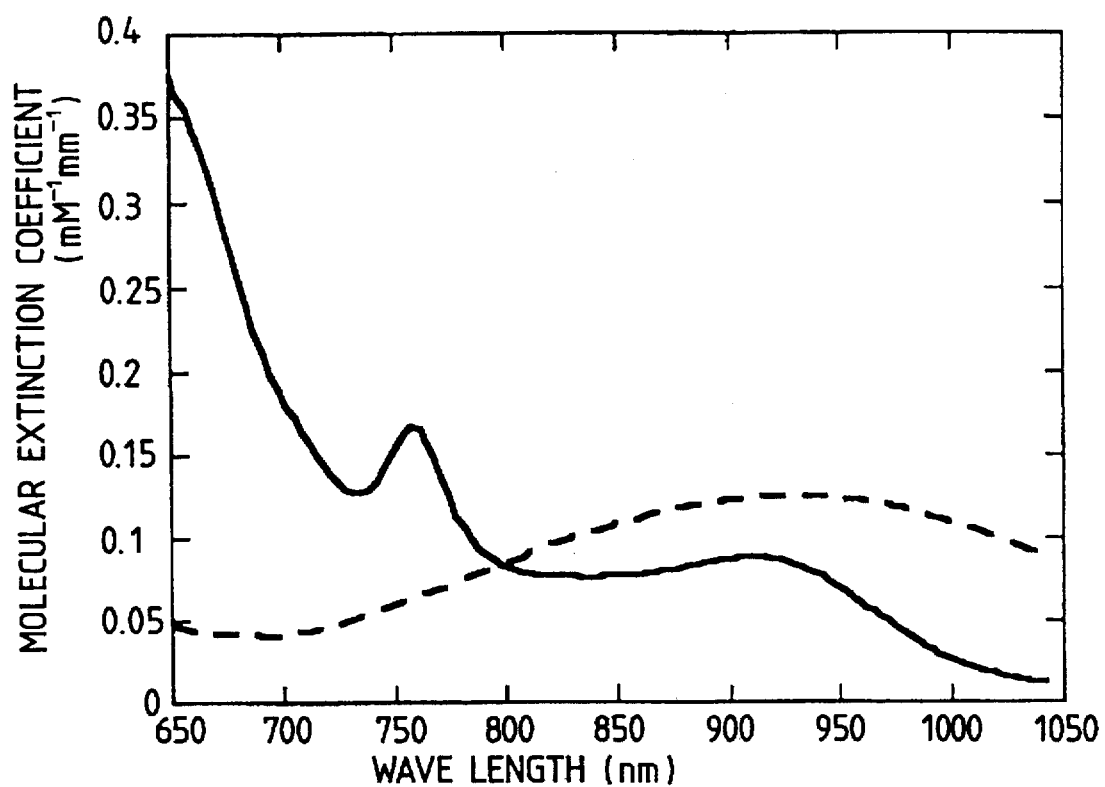
FIG. 28 shows wavelength spectra of the absorption coefficients of oxygenated hemoglobin and deoxygenated hemoglobin.

FIG. 28 shows wavelength spectra of the molecular extinction coefficients of Hb and $HbO_2$ used for solving the simultaneous equations. The graphs shown in the figure are drawn from numerical data extracted from a document written by S. Wray et al. with the title "Characterization of the Near-infrared Absorption Spectra of Cytochrome aa3 and Hemoglobin for the Non-invasive Monitoring of Cerebral Oxygenation," Biochem. Biophys. Acta 933, pages 184–192 (1988). A solid line shown in the figure represents the wavelength spectrum of Hb's molecular extinction coefficient whereas a dotted line represents the wavelength spectrum of $HbO_2$'s molecular extinction coefficient. Wavelength spectra of molecular extinction coefficients of absorbers like the ones shown in the figure are stored in a storage device of the computer for later use in finding an absorption coefficient for a wavelength of an incident light used in the measurement. Even in the case of a tissue of a human body other than the head such as a human-body member like, for example, the breast used as an object, it is also possible to find spatial distributions of Hb and $HbO_2$ in the object by using a special optical-fiber fixing holder and near-infrared lights as incident lights.

In addition, in the case of $\gamma$ types of absorbers existing in an object, spatial distributions of concentrations of the $\gamma$ absorbers can thus be found in a similar way by utilizing ($\gamma$+1) incident lights which have wavelengths different from each other. For example, spatial distributions of concentrations of Hb, $HbO_2$ and myoglobin in a muscle can be found by using four kinds of incident light having wavelengths different from each other.

Figure 29:
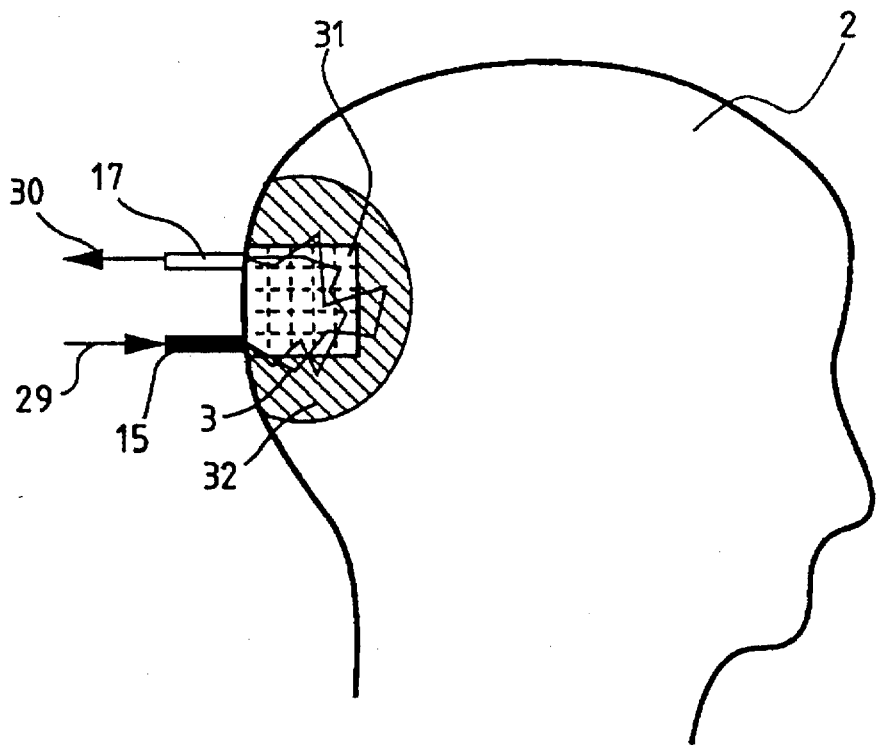
FIG. 29 is a diagram showing an example of application of the present invention to an area of a portion of a human body.

A technique for finding spatial distributions of absorber concentrations in an area of part of an object is described by referring to FIG. 29. The figure is a diagram showing how to find spatial distributions of absorber concentrations in a region of interest 31 in a portion of the object which is the head of a human body. Having a cubic shape with a side length of 25 mm, the region of interest 31 shown in FIG. 29 is divided into a total of 125 (5×5×5) volume elements. The absorber concentrations in each of the volume elements are found. A light 29 radiated from an incident-light optical fiber 15 provided in close proximity to the region of interest 31 is applied to an object 2. The light is scattered in the object 2 before arriving at a light-detection optical fiber 17 also located in close proximity to the region of interest 31. The light is then detected by a detector 30. Since the detector is placed on the same side as the incident position, the light detected thereby is a reflected light. It should be noted that since a photon path 3 from the incident-light optical fiber 15 to the light-detection optical fiber 17 also extends to the outside of the region of interest 31, spatial distributions of the absorber concentrations must be found for an area 32 except the region of interest to which the light arrives. The area 32 is referred to hereafter as an observation area. The shape of the observation area 32 is determined in advance by using a technique such as the simulation using the Monte Carlo method or the simulation based on a diffusion equation. Typically, an observation area 32 is determined so as to contain an area passed through by 95% of the light arriving at the light-detection optical fiber 17 from the incident-light optical fiber 15.

Spatial distributions of the absorber concentrations in the observation area 32 can be found using a technique of dividing the observation area 32 into volume elements as is the case with the region of interest 31 or a technique of treating part of the observation area 32 outside the region of interest 31 as one volume element. The former is virtually the same as the latter except that the number of volume elements in the former is different from that in the latter. In this embodiment, part of the observation area 32 outside the region of interest 31 is treated as one volume element. Thus, the number of volume elements in the observation area 32, for which spatial distributions of the absorber concentrations are to be found, is 126. For this reason, it is necessary to provide at least 126 different measurement-position sets or positional relations between incident and detection positions. The number of ways in which measurement-position sets can be arranged is infinite. By installing typically at least 9 incident-light optical-fiber lines 15 and at least 16 light-detection optical fibers 17 in close proximity to the region of interest 31 shown in FIG. 29, at least 126 (=9×14) measurement-position sets can be arranged. The intensity of a detected light 30 passing through the object 2 can be measured for each measurement-position set by a device having a configuration like the one shown in FIG. 25, allowing the spatial distribution of the absorber concentration in the observation area 32 to be found in accordance with the procedure shown by the flowcharts of FIGS. 15, 16 and 17. It should be noted that, in order to find the concentrations of $HbO_2$ and Hb in each volume element using near-infrared beams as incident lights, three wavelengths of the incident lights are required. In addition, when a matrix A expressing a spatial distribution of averaged photon-path lengths is calculated, the external shape of the observation area 32 is input. Since the external shape of the observation area 32 can be found in advance, the matrix A expressing a spatial distribution of averaged photon-path lengths can also be found in advance and stored in memory.

A procedure referred to simply as a rotating and transforming Monte Carlo method is described below in detail by referring to diagrams. In this procedure, a plurality of photon paths starting from arbitrary incident positions and ending at arbitrary detection positions in an object are calculated and temporarily stored in memory as photon-path data which is then used for creating a matrix A expressing a spatial distribution of averaged photon-path lengths. A plurality of photon paths starting from arbitrary incident positions and ending at arbitrary detection positions are found by calculation by means of the Monte Carlo method which simulates optical scattering in the object by using scattering characteristics of the object. A technique adopted by Wilson et al. explained earlier is a most representative example of the conventional Monte Carlo method used for calculating a photon path by simulating the classic optical scattering phenomenon. A plurality of photon paths starting from arbitrary incident positions and ending at arbitrary detection positions in an object could be calculated on the spot whenever necessary by using the conventional Monte Carlo method. However, such calculation would take much time and is, hence, not practical. In the present invention, photon-path data is stored in advance and, by utilizing the stored photon-path data, the calculation can be carried out at a speed about 100 times higher or more than that of the conventional technique for calculating photon paths on an as-needed basis.

Figure 30:
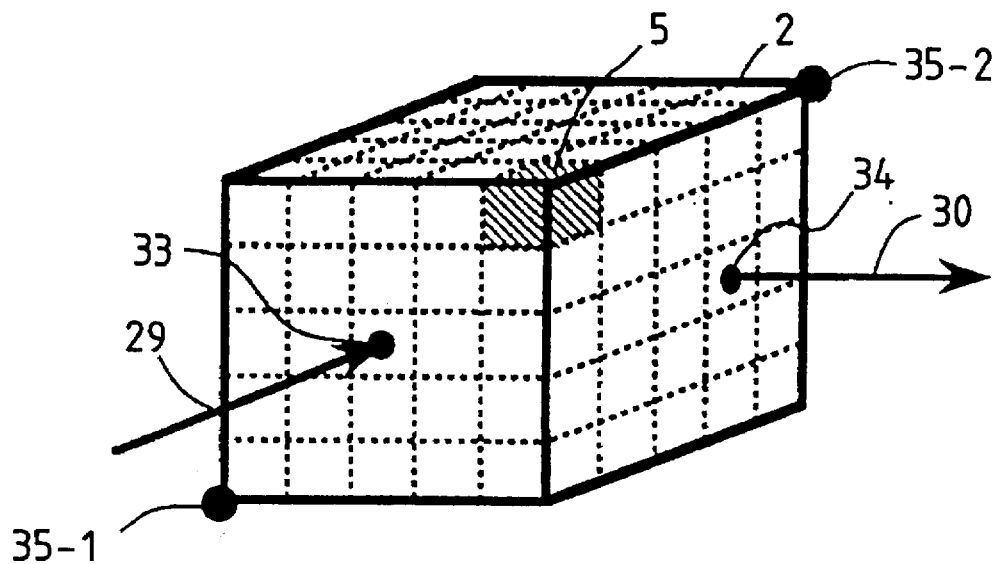
FIG. 30 is a diagram showing a typical object to which the rotating and transforming Monte Carlo method is applied in accordance with the present invention.
Figure 31:
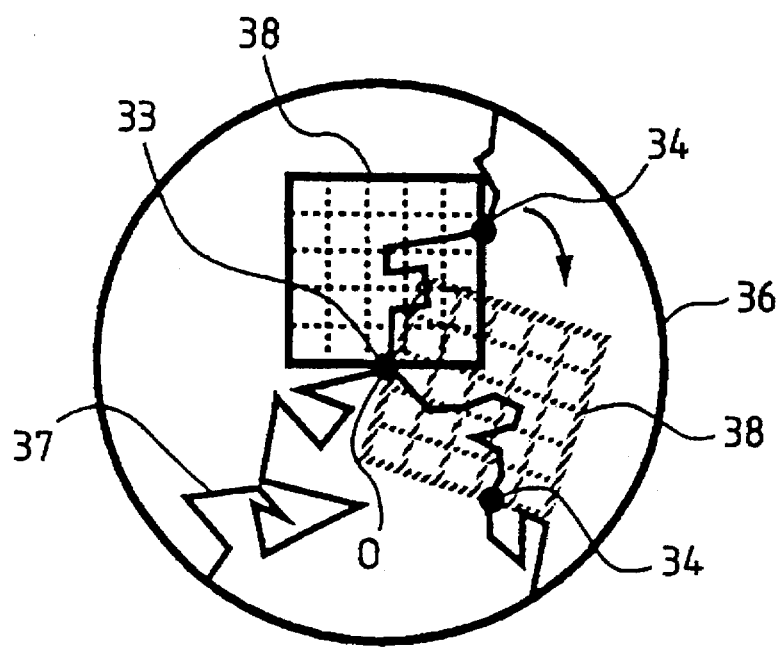
FIG. 31 is a diagram used for explaining the concept of the rotating and transforming Monte Carlo method adopted by the present invention.

The following description of the method is based on an object having a cubic shape like the one shown in FIGS. 12 or 13. FIG. 30 is a diagram showing the shape of an object assumed in order to explain the rotating and transforming Monte Carlo method and relative positional relations between incident positions 33 radiating radiated lights 29 and detection positions 34 for detecting detected lights 30. A representative example of a procedure for calculating a plurality of photon paths starting from the incident positions 33 and ending at the detection positions 34 shown in FIG. 30 using the rotating and transforming Monte Carlo method is explained as follows. A cubic object 2 shown in the figure is hypothetically divided into 5×5×5 volume elements 5 each of which is also cubic. FIG. 31 is a diagram used for explaining the concept of the rotating and transforming Monte Carlo method. For the sake of simplicity, only a cross section including an incident position 33 and a detection position 34 along with a photon path 37 existing on the cross section is shown in the figure. First of all, a spherical model scattering medium 36 is created in a computer. The spherical model scattering medium 36 has a radius equal to the maximum value of a distance from an arbitrary point to another arbitrary one in the object 2. In the case of an object shape shown in FIG. 30, it is the distance from a vertex 35-1 to a vertex 35-2. In FIG. 30, however, the spherical model scattering medium 36 itself is not shown. A photon radiated from the center O of the spherical model scattering medium 36 undergoes multiple scattering repeatedly in accordance with equivalent scattering characteristics of the object 2, arriving at the boundary surface of the spherical imiginary scattering medium 36. Here, by scattering characteristics, the scattering coefficient and the phase function of the object described earlier are meant.

By storing scattering points of a photon on a photon path up to its arrival at the boundary surface of the spherical model scattering medium 36 in memory as photon-path data, a photon path 37 traced by the photon in the spherical model scattering medium 36 can be reproduced. After a radiated photon has arrived at the boundary surface, photon paths traced by a plurality of photons can be obtained by repeating the same process. After a photon-path count sufficient for substantially ensuring the statistical accuracy has been reached, a model object 38 having the same external shape as that of the object 2 is created as shown in FIG. 31. An incident position 33 and a detection position 34 corresponding to the incident position 33 and the detection position 34 on the object 2 are set on the imiginary object 38. Subsequently, the incident position 33 of the model object 38 is placed at the center position of the spherical model scattering medium 36 and the model object 38 is rotated with the center O of the spherical model scattering medium 36 taken as a center of revolution. In this way, the position of the photon path relative to the imaginary object 38 can be changed to find a cross-point of a locus of the detection point 34 on the model object 38 and the photon path stored in the memory in the previous process. Then, coordinates of scattering points for reproducing a photon path starting from the center O and ending at the cross-point are transformed into coordinates set on the model object 38. That is to say, a line segment connecting the incident position 33 to the detection position 34 on the model object 38 is rotated with the center O of the spherical model scattering medium 36 taken as a center of revolution and a cross-point of the locus traced by the detection position 34, one end of the line segment, and the photon path stored in the memory is found. The same operation is repeated for each piece of photon-path data stored in the memory to find a plurality of photon paths starting from the incident position 33 and ending at the detection position 34 on the model object 38. For example, when the processing of a photon path has been completed, the model object 38 is rotated around the center O in a direction indicated by an arrow as shown in FIG. 31 in order to process the next piece of photon-path data. From photon-path data for photon paths staring from the incident point 33 and ending at the detection point 34 on the spherical model scattering medium 36 or data of scattering points on the photon paths, which data has been found earlier, a photon-path length can be calculated for each volume element. The photon-path length for each volume element is stored in memory to be used later in the calculation of a spatial distribution of averaged photon-path lengths for a measurement-position set of the incident and detection positions 33 and 34 on the object 2 using Equation (42). A two-dimensional application of the rotating and transforming Monte Carlo method has been explained so far. It is needless to say that a similar process can be carried out for a three-dimensional application. Also in the case of an object having a general shape, the object is divided into a plurality of spatial elements and a model object having the same external shape as that of the real object is created in the processing device. The same processing described above is then carried out, allowing a spatial distribution of averaged photon-path lengths, which photon paths connect an incident position to a detection position set on the object having an arbitrary shape, to be calculated by using Equation (42)

Figure 17:
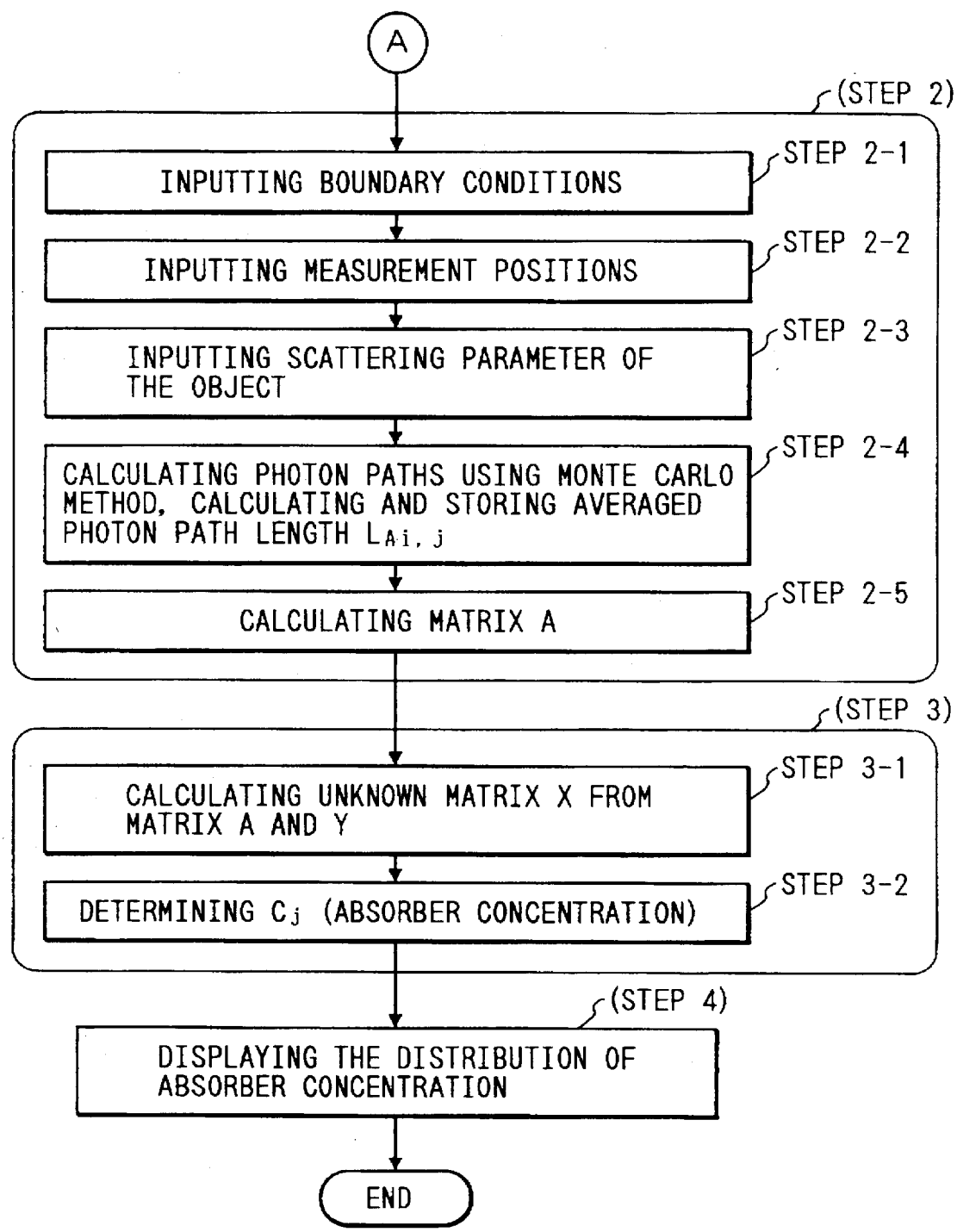
Figure 32:
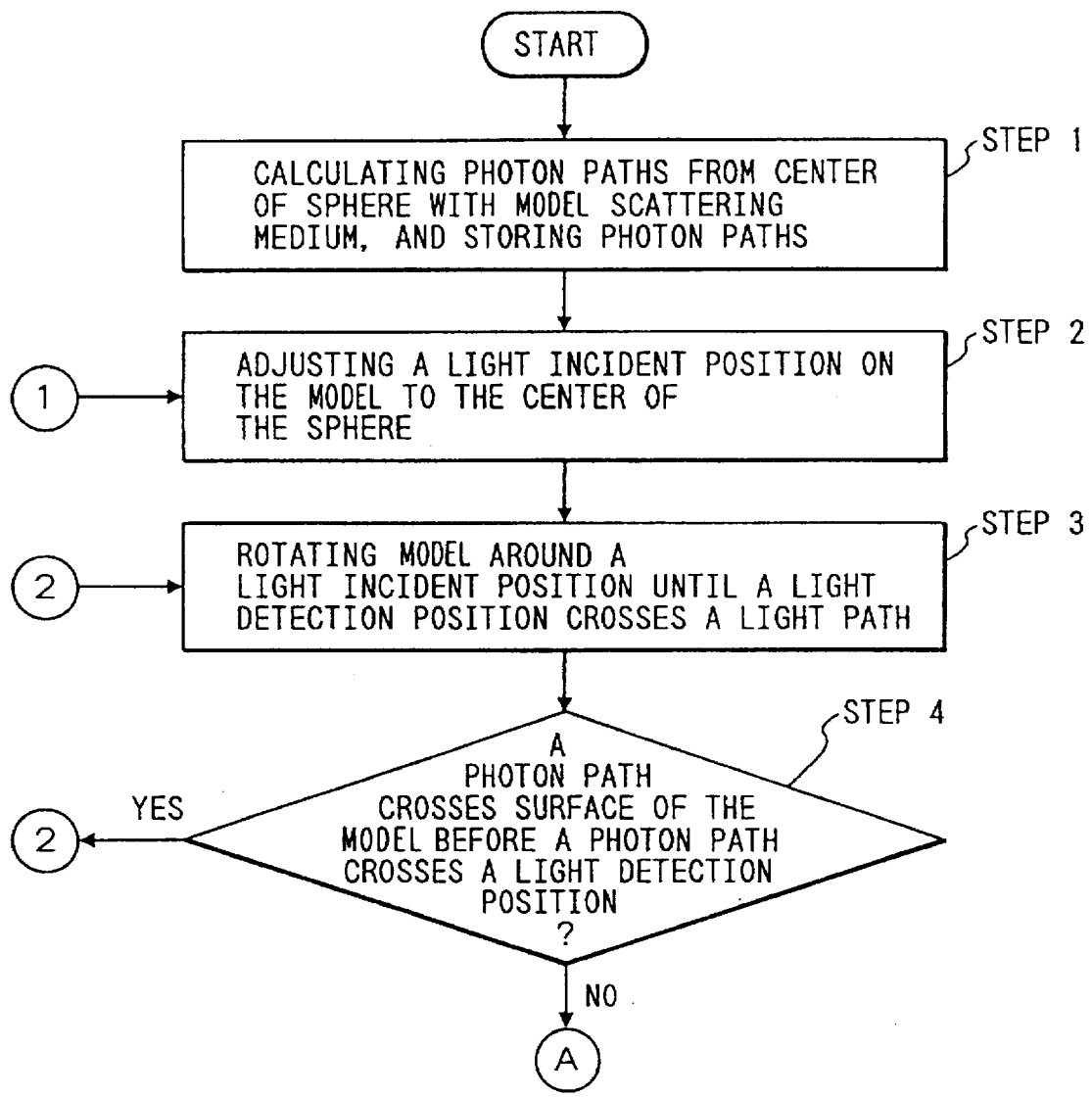
FIGS. 32 and 33 show a flowchart of a procedure for finding a spatial distribution of averaged photon-path lengths by using the rotating and transforming Monte Carlo method in accordance with the present invention.
Figure 33:
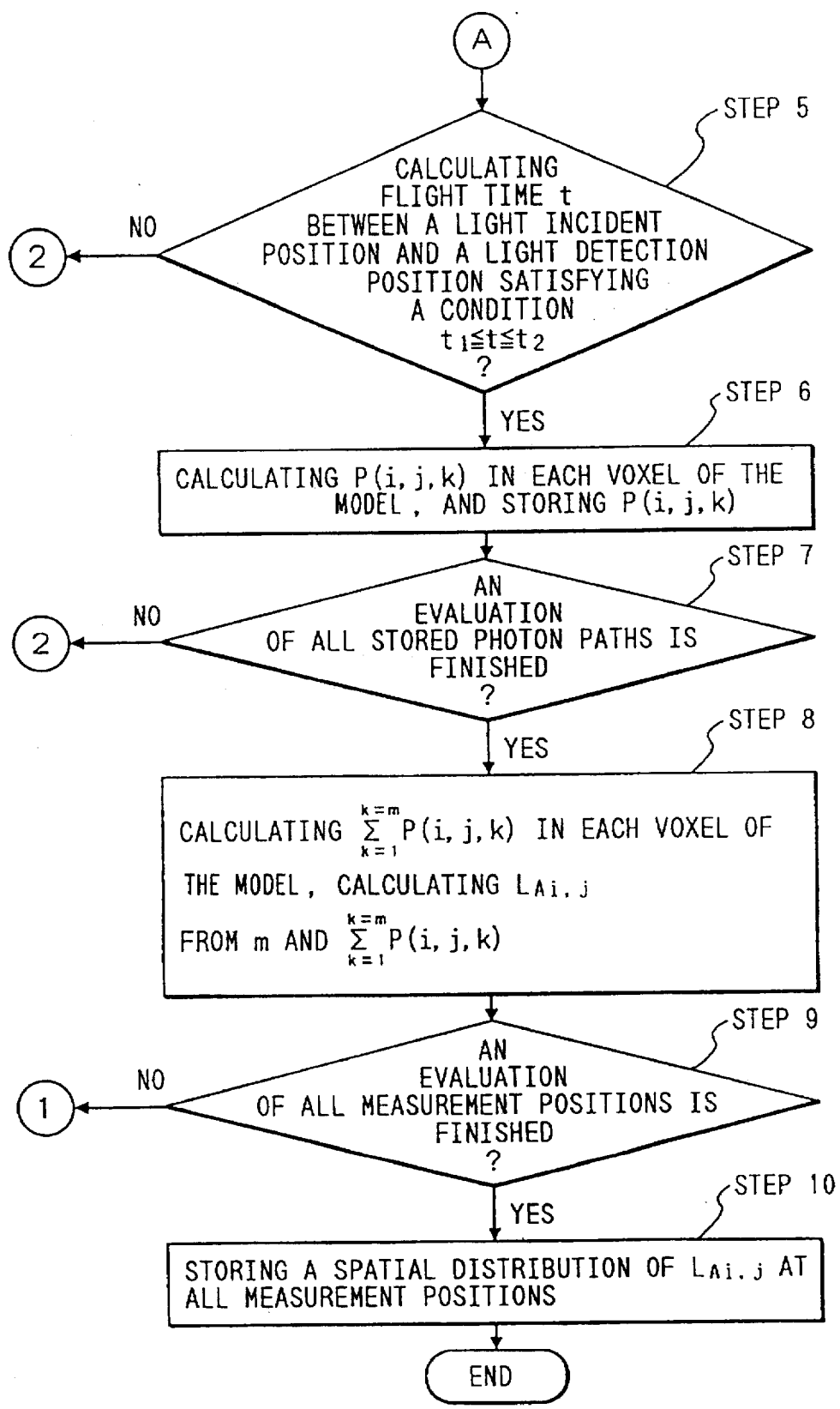

A flowchart of the procedure described above is shown in FIGS. 32 and 33. Each step in the flowchart is explained in detail as follows. It should be noted that, as shown in FIG. 17, data representing the external shape of an object and scattering characteristics of the object have already been input.

step 1: Any arbitrary two points are taken on the surface of the object and a spherical model scattering medium 36 with a radius equal to a maximum of distances from one of the two points to the other is created. A photon is radiated from the center of the spherical model scattering medium 36 and data of a photon path up to a point on the boundary surface of the spherical model scattering medium 36 from which the photon is emitted is stored in memory. Data of at least 1,000 photon paths needs to be stored to substantially ensure the statistical accuracy. The scattering characteristics of the spherical model scattering medium 36 reflect those of the object.

step 2: An model object divided into volume elements is created. An incident position corresponding to an incident position on the object is set on the model object. The incident position on the model object is placed at the center of the spherical model scattering medium.

step 3: A photon path is selected arbitrarily from the photon-path data stored at the step 1. The model object is rotated so that the locus of a detection position on the model object, which detection position is set at the same location as the incident position of the object, crosses the selected photon path. The center of the spherical model scattering medium, that is, the incident position is taken as the center of the rotation. A photon path should never be selected more than once at this step.

step 4: Determination is made as to whether or not the photon path connecting the incident position to the detection position crosses the boundary surface of the spherical model scattering medium. If the photon path crosses the boundary surface, the flow returns to the step 3. If the photon path does not cross the boundary surface, on the other hand, the flow proceeds to a step 5.

step 5: A time t required by a photon to travel from the incident position to the detection position is computed from a total photon-path length to determine whether or not the time t satisfies a detection-time condition $t_1 \leq t \leq t_2$. If the condition is satisfied, the flow returns to the step 3 to carry out processing for the next piece of photon-path data. If the condition is not satisfied, on the other hand, the flow proceeds to a step 6.

step 6: Coordinates of scattering points on the photon-path starting from the incident position and ending at the detection position are transformed from a coordinate system of the spherical model scattering medium into a coordinate system on the model object. Then, a photon-path length p(i, j, k) for each volume element is calculated and stored in memory.

step 7: Determination is made as to whether or not the processing at each of the above steps has been completed for all pieces of photon-path data. If not completed, the flow returns to the step 3. If completed, on the other hand, the flow proceeds to a step 8.

step 8: The cumulative number (m) of photon paths processed up to this step corresponds to the denominator of the right-hand side of Equation (38) and is equal to the number of photons arriving at the detector during the time period between arrival times $t_1$ and $t_2$. A cumulative photon-path length for each volume element, the numerator of the right-hand side of Equation (38), is calculated from the photon-path length p(i, j, k) for each volume element and then divided by the cumulative number (m) of photon paths. At this step, an averaged photon-path length $L_{Aij}$ (or a spatial distribution of averaged photon-path lengths) in a jth volume element for an ith measurement-position set (or an ith pair of incident and detection positions) is calculated. The flow then proceeds to a step 9 in order to calculate a spatial distribution of averaged photon-path lengths for a different measurement-position set.

step 9: Determination is made as to whether processing has been completed for all measurement-position sets (all pairs of incident and detection positions). If the processing has not been completed, the flow returns to the step 2. If the processing has been completed, on the other hand, the flow proceeds to a step 10.

step 10: The spatial distribution of averaged photon-path lengths for all measurement-position sets is stored in the memory. In the procedure shown by the above flowchart, it is not always necessary to carry out the processing for all measurement-position sets. In the case of a plurality of different measurement-position sets (or pairs of incident and detection positions) having a geometrically equivalent relation, a measurement-position set is selected from them. For the selected measurement-position set, a photon path is then found. By transforming coordinates in such a way that the found photon path coincides with other geometrically equivalent measurement-position sets, the processing time can thus be shortened. This processing can be performed at the step 6. For example, a measurement-position set in FIG. 30 in which a point $(3, 3)_{P1}$ is the incident position 33 and a point $(4, 3)_{P2}$ is the detection position 34 is considered to be geometrically equivalent to a measurement-position set for the incident position at a point $(3, 3)_{P1}$ and a detection position at a point $(4, 3)_{P4}$ on the surface P4 parallel to the surface P2 and other measurement-position sets. For a definition of the surface Pi, refer to FIG. 9.

Figure 34:
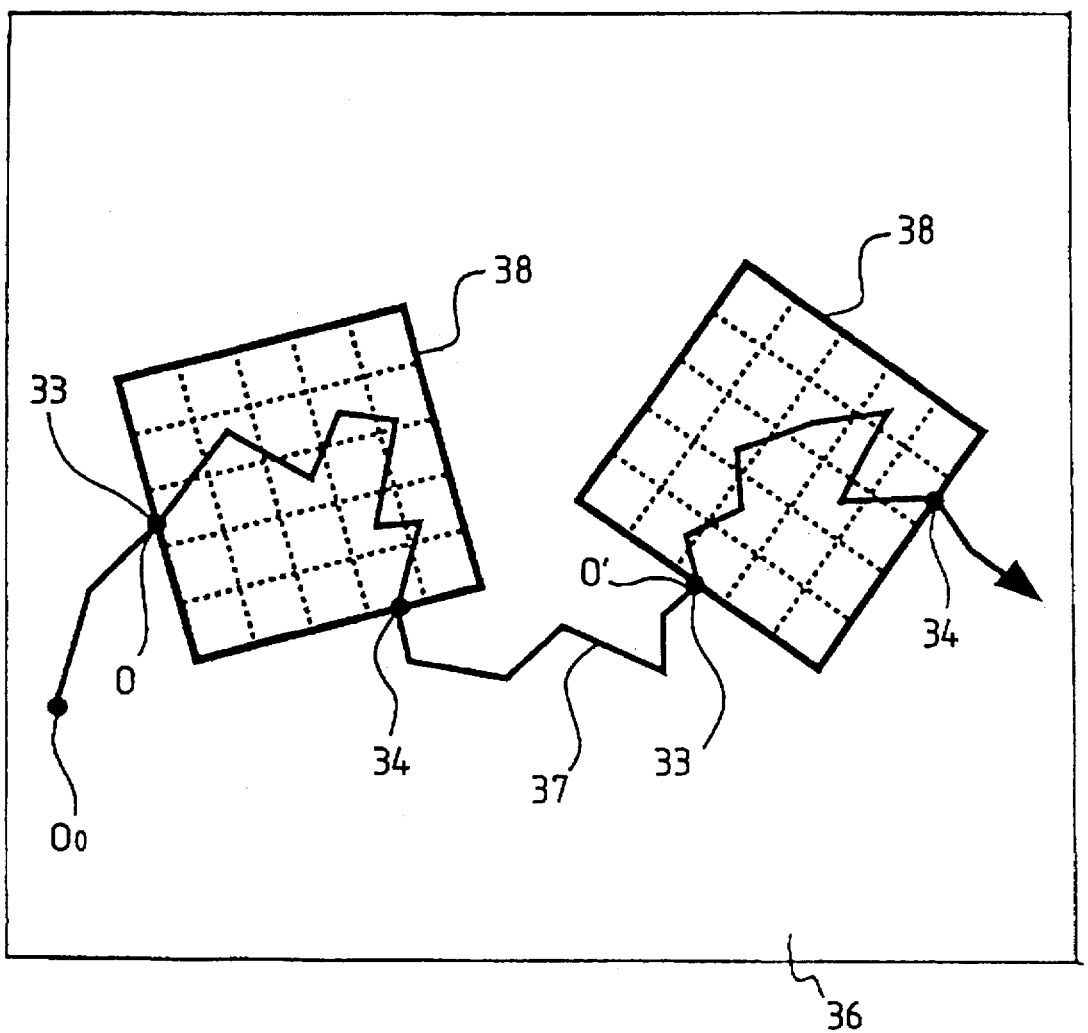
FIG. 34 is a diagram used for explaining the concept of the rotating and transforming Monte Carlo method adopted by the present invention.

The rotating and transforming Monte Carlo method has been described above. By using the same way of thinking, a plurality of scattering points traced by a photon originating from a point ($O_0$) in a model scattering medium 36 shown in FIG. 34 are stored in memory in advance as photon-path data, allowing a photon path 37 to be reproduced. It should be noted that, if the model scattering medium 36 occupies a space having a sufficiently large size, the model scattering medium 36 can have any arbitrary shape. This technique is known as the transforming and rotating Monte Carlo method. Note that, much like FIG. 31, FIG. 34 shows only a cross section including the incident and detection points 33 and 34 shown in FIG. 30 for the sake of simplicity and the photon path 37 exists on the cross section. An incident position 33 on a model object 38 in the model scattering medium 36 is located at any arbitrary position O on the model scattering medium 36. The model object 38 is rotated with the point O on the model scattering medium 36 taken as a center of rotation to change the position of the model object 38 relative to the photon path 37. A cross-point of a locus of the detection point 34 on the model object 38 and the photon path 37 stored in the memory is found. Then, coordinates of scattering points for reproducing a photon path starting from the rotation center O and ending at the cross-point are transformed into coordinates set on the model object 38 and a photon-path length p(i, j, k) for each volume element is then calculated and stored in the memory. Subsequently, the position of the incident point 33 is moved from the point O to a point O' along the photon path and the same processing is carried out. It is desirable to set the distance from the point O to the point O' at a value greater than the distance from the incident point 33 to the detection point 34. Other processings are the same as those of the rotating and transforming Monte Carlo method explained earlier. A two-dimensional application of the rotating and transforming Monte Carlo method has been explained so far. It is needless to say that a similar process can be carried out for a three-dimensional application. Also in the case of an object having a general shape, a spatial distribution of averaged photon-path lengths between incident and detection positions set on the object can be calculated by using Equation (38).

We claim:

1. An imaging method for spatial distributions of concentrations of absorbers distributed in an object comprising:
   a radiation step of applying pulsating or continuous light radiated from predetermined incident positions with predetermined wavelengths to said object comprising a scattering medium containing said absorbers; and
   a detection step of detecting intensities of light passing through said object at predetermined detection positions,
   said imaging method further comprising the steps of:
   a first step of finding a plurality photon paths for a plurality of pairs of said incident and detected positions of a model with similar dimensions to the object but without absorbers starting at said incident positions and ending at said detected positions;
   a second step of finding averaged photon-path lengths of said photon paths starting at said incident positions and ending at said detection positions in said model only by simulation;
   a third step of finding spatial distributions of absorber concentrations from said averaged photon-path lengths, radiated intensities of said radiated light applied to said object, detected intensities of light detected at said detection positions and optical constants of said absorbers for said radiated light applied to said object; and a fourth step of displaying said spatial distributions of said absorber concentrations.

2. An imaging method for spatial distributions of concentrations of absorbers according to claim 1, wherein said third step comprises the steps of:

creating a measurement matrix representing a ratio of said radiated intensity to said detected intensity for one of said pairs;

creating a spatial distribution matrix expressing a spatial distribution of averaged photon-path lengths using data of said averaged photon-path corresponding to said pairs; and finding said absorber concentrations by use of said measurement matrix and said spatial distribution matrix.

3. An imaging method for spatial distributions of concentrations of absorbers according to claim 2, wherein light radiated to said object at said radiation step have a plurality of wavelengths ranging from 400 nm to 2,000 nm and differences in value between any two of said wavelengths are all made smaller than 100 nm.

4. An imaging method for spatial distributions of concentrations of absorbers according to claim 2, wherein a number of light radiated to said object at said radiation step is greater by unity than the number of absorbers and said radiated light have wavelengths different from each other.

5. An imaging method for spatial distributions of concentrations of absorbers according to claim 1, wherein said first step comprises the step of carrying out coordinate transformation for finding data of said photon paths for a pair (j-i) from data of said photon paths for a pair (i-j) by swapping locations of said (i) and said (j) for each other, where said pair (i-j) other pairs having positional relationship being mutually equivalent to said pair (i-j) on boundary condition of said model.

6. An imaging method for spatial distributions of concentrations of absorbers according to claim 1, wherein said first step includes the step of simulating said step of finding a plurality of photon paths by means of a Monte Carlo method using a random number and a function expressing scattering-angle dependence relating a spatial coordinate position of a current scattering point to that of a next scattering point among a plurality of points scattering a photon from a point to another and wherein said Monte Carlo method is used for simulating a photon path traced by said photon originating from a point in model scattering medium having virtually the same scattering coefficient as that of said object and a size large enough to contain a model object.

7. An imaging method for spatial distributions of concentrations of absorbers according to claim 6, further comprising a step of storing spatial coordinate positions of said scattering points expressing said photon paths in memory.

8. An imaging method for spatial distributions of concentrations of absorbers according to claim 1, wherein said optical constants are absorption coefficients of said absorbers for wavelengths of light radiated to said object at said radiation step.

9. An imaging method for spatial distributions of concentrations of absorbers according to claim 1, wherein at said first step of finding said photon paths, each of said photon paths traced by a photon emitted from a predetermined point in a model scattering medium having virtually the same scattering coefficient as that of said object is simulated by a simulation using a Monte Carlo method.

10. An imaging method for spatial distributions of concentrations of absorbers according to claim 9, wherein said simulation comprises:

a step of transforming either spatial coordinates of said scattering points representing points representing said photon paths or spatial coordinates expressing the shape of said model in such a way that said incident position in said object is made to coincide with a point on an arbitrary photon path in said model scattering medium and said detection position in said model is crossed with an arbitrary point on said photon path; and a step of detecting photon paths starting from said incident positions in said model and ending at said model.

11. An imaging method for spatial distributions of concentrations of absorbers according to claim 10, wherein said model scattering medium is a sphere having a radius equal to or greater than a maximum distance from any arbitrary point to another arbitrary one in said model and said predetermined point is set at the center of said sphere, from which point a plurality of photons are emitted.

12. An imaging method for spatial distributions of concentrations of absorbers according to claim 1, wherein a space expressing the shape of said object is divided into a plurality of volume elements, in each of which, said averaged photon-path length is found and, by assuming that concentrations of said absorbers in each of said volume elements are uniform, concentrations of said absorbers in each of said volume elements are found.

13. An imaging method for spatial distributions of concentrations of absorbers according to claim 12, wherein the number of pairs of said incident positions and said detection positions is greater than the total number of said volume elements.

14. An imaging method for spatial distributions of concentrations of absorbers according to claim 12, wherein at said first step, a space expressing the shape of said model is divided into a plurality of volume elements in the same way as said space expressing the shape of said object is divided into a plurality of volume elements and said first step comprises the step of finding said photon paths in said model between said volume elements having said incident positions set therein and said volume elements having said detection positions set therein by means of a Monte Carlo method using a scattering coefficient of said object and parameters representing scattering-angle dependence of photon scattering in said object for each of said various pairs of said incident and detection positions.

15. An imaging method for spatial distributions of concentrations of absorbers according to claim 14, wherein said second step finds an averaged photon-path length for each of said volume elements of said model by averaging lengths of photon paths in each of said pairs.

16. An imaging method for spatial distributions of concentrations of absorbers according to claim 14, which further comprises a shape measuring step of measuring the external shape of said object to give measurement data used as a base for providing coordinate data representing a space of the shape of said model or coordinate data representing a space of a shape resembling said model.

17. An imaging method for spatial distributions of concentrations of absorbers according to claim 12, wherein a space expressing the shape of said model is divided into a plurality of volume elements in the same way as said space expressing the shape of said object is divided into a plurality of volume elements and said third step comprises:

creating a measurement matrix each representing a ratio of said radiated intensity to said detected intensity;

finding said photon paths in said model between said volume elements having said incident positions set therein and said volume elements having said detection positions set therein by means of a Monte Carlo method using a scattering coefficient of said object and parameters representing scattering-angle dependence of photon scattering in said object for each of said various pairs of said incident and detection positions; and creating a spatial distribution matrix expressing a spatial distribution of averaged photon-path lengths representing said averaged photon path lengths for said pairs found from said photon paths, wherein absorber concentrations are found from said measurement matrix and said spatial distribution matrix expressing a spatial distribution of averaged photon-path lengths.

18. An imaging method for spatial distributions of concentrations of absorbers according to claim 17, further comprising the step of storing said matrix in a storage means.

19. An imaging method for spatial distributions of concentrations of absorbers according to claim 17, wherein the intensity of a light passing through said object is measured by using a time-resolving technique at said detection step and the detected intensity used in the step of creating a measurement matrix is obtained by integrating results of measuring the intensity of said light by using said time-resolving technique over a predetermined period of time.

20. An imaging method for spatial distributions of concentrations of absorbers distributed in an object having a predetermined shape and a predetermined scattering coefficient, including a radiation step of applying pulsating or continuous light radiated from predetermined incident positions with predetermined wavelengths to said object comprising a scattering medium containing said absorbers and a detection step of detecting intensities of light passing through said object at predetermined positions, said imaging method further comprising the steps of:

a first step of finding a plurality of photon paths for a plurality of pairs of said incident and detected positions of a model with similar dimensions to the object but without absorbers starting at said incident positions and ending at said detected positions;

a second step of finding averages photon-path lengths of said photon paths starting at said incident positions and ending at said detection positions in said model by a simulation method;

a third step of creating a spatial distribution matrix expressing a spatial distribution of averaged photon-path lengths using data of said averaged photon-paths corresponding to said pairs; and a fourth step of storing said spatial distribution matrix in a storage means;

a fifth means of finding spatial distributions of absorber concentration from said average photon-path lengths, radiated intensities of said radiated light applied to said object, detected intensities of light detected at said detection positions and optical constants of said absorbers for said radiated light applied to said objects; and a sixth step of displaying said spatial distributions of said absorber concentration.

21. An imaging method for spatial distributions of absorber concentrations according to claim 20 wherein said fifth step comprises the steps of:

creating a measurement matrix representing a ratio of said radiated intensity to said detected intensity corresponding to said pairs; and finding absorber concentrations by use of said measurement matrix and said spatial distribution matrix stored in said storage means.

22. An imaging method for spatial distributions of concentrations of absorbers having a predetermined shape and a predetermined scattering coefficient, including a radiation step of applying pulsating or continuous light radiated from predetermined wavelengths to said object comprising a scattering medium containing said absorbers and a detection step of detecting intensities of light passing through said object at predetermined positions, said imaging method comprising the steps of:

a first step of finding a plurality photon paths for a plurality of pairs of said incident and detected positions of a model with similar dimensions to the object but without absorbers starting at said incident positions and ending at said detected positions;

a second step of finding average photon-path lengths of said photon paths starting at said incident positions and ending at said detection positions in said model by a simulation method;

a third step of finding spatial distributions of absorber concentration from said average photon-path lengths, radiated intensities of said radiated light applied to said object, detected intensities of light detected at said detection position and optical constants of said absorbers for said radiated light applied to said object;

a fourth step of displaying said spatial distributions of said absorber concentration, wherein the fourth step comprises the steps of:

creating a measurement matrix representing a ratio of said radiated intensity to said detected intensity for one of said pairs;

creating a spatial distribution matrix expressing a spatial distribution of averaged photon-path lengths using data of said averaged photon-path corresponding to said pairs; and finding said absorber concentrations from said measurement matrix and said spatial distribution matrix.

23. A measuring method measuring for spatial distributions of concentrations of absorbers in an object being a light scattering medium including light absorbing material by a radiation step of applying pulsating or continuous light radiated from predetermined incident positions to the object, a detection step of detecting intensities of light passing through said object at predetermined detection positions, and a signal processing step of calculating concentrations of said absorbers distributed in said object by using the intensities of light, said measuring method further comprising the steps of:

a first step of finding a plurality photon paths starting at said incident portions and ending at said detected positions of each of volume elements forming a model with similar dimensions to the object but without absorbers by simulation, and each of volume elements forming said model has spatial dimensions similar to those of each of volume elements forming said object;

a second step of finding average photon-path lengths of said photon paths starting at said incident positions and ending at said detection positions for each of said volume elements forming said model;

a third step of finding an absolute value of absorber concentration of each of volume elements forming said object from said average photon-path lengths, radiated intensities of said radiated light applied to said object, detected intensities of said radiated light applied to said object, detected intensities of light detected at said detection positions and optical constants of said absorbers for said radiated light applied to said object; and said third step comprising:

creating a measurement matrix representing a ratio of said radiated intensity to said detected intensity for each of said pairs of said radiated intensity and detected intensity;

creating a spatial distribution matrix expressing a spatial distribution of averaged photon-path lengths using data of said photon-paths corresponding to said pairs; and finding said absolute value of absorber concentrations of each of volume elements forming said object by use of said measurement matrix and said spatial distribution matrix.

24. A measuring method for spatial distributions of concentrations of absorbers according to claim 23, wherein said plurality of photon paths obtained in said first step is stored in memory means, and said third step uses said plurality photon paths stored in said memory means.

25. A measuring method for spatial distributions of concentrations of absorbers according to claim 23, wherein said simulation comprises a step of transforming either spatial coordinates of said scattering points representing points representing said photon paths or spatial coordinates expressing the shape of said model in such a way that said incident position in said object is made to coincide with an arbitrary point on an arbitrary photon path in said scattering medium and said detection position in said model is crossed with another arbitrary point on said photon path; and a step of detecting photon paths starting from said incident positions in said model to said detection positions ending in said model.

26. A measuring method for spatial distributions of concentrations of absorbers according to claim 23, wherein said scattering medium is a sphere having a radius equal to or greater than a maximum distance from any arbitrary point to another arbitrary one in said model and one of said any arbitrary point is set at the center of said sphere, from which point a plurality of photons are emitted.

* * * * *